(12) United States Patent
Yamasaki et al.

(10) Patent No.: US 7,954,624 B2
(45) Date of Patent: Jun. 7, 2011

(54) SHUTTLE TYPE CONVEYING DEVICE, MICROPLATE FEEDING AND COLLECTING DEVICE, PICKUP DEVICE FOR MICROPLATE, CASSETTE FOR MICROPLATE, AND SHELF FOR CONTAINING MICROPLATE

(75) Inventors: Yukito Yamasaki, Tukuba (JP); Teruyoshi Munakata, Tukuba (JP)

(73) Assignees: Rorze Corporation, Fukuyama-shi (JP); Is Technology Japan, Inc., Tukuba-shi (JP)

( * ) Notice: Subject to any disclaimer, the term of this patent is extended or adjusted under 35 U.S.C. 154(b) by 112 days.

(21) Appl. No.: 12/300,647

(22) PCT Filed: May 16, 2006

(86) PCT No.: PCT/JP2006/309753
§ 371 (c)(1),
(2), (4) Date: Jan. 22, 2009

(87) PCT Pub. No.: WO2007/132526
PCT Pub. Date: Nov. 22, 2007

(65) Prior Publication Data
US 2009/0287345 A1 Nov. 19, 2009

(51) Int. Cl.
*B65G 17/12* (2006.01)
(52) U.S. Cl. .................... 198/468.6; 198/468.9
(58) Field of Classification Search ............... 198/346.2, 198/346.3, 468.6, 468.9; 414/564, 749.1
See application file for complete search history.

(56) References Cited

U.S. PATENT DOCUMENTS

| | | | | |
|---|---|---|---|---|
| 4,534,695 A | * | 8/1985 | Stump et al. | 198/468.6 |
| 4,669,607 A | * | 6/1987 | Mason | 198/774.1 |
| 5,203,445 A | * | 4/1993 | Shiraiwa | 198/464.3 |
| 7,070,380 B2 | * | 7/2006 | Ito et al. | 198/468.6 |
| 2006/0210431 A1 | | 9/2006 | Higuchi et al. | |

FOREIGN PATENT DOCUMENTS

| | | |
|---|---|---|
| EP | 1 070 674 A2 | 1/2001 |
| JP | 63-218080 | 9/1988 |
| JP | 4-70568 | 6/1992 |
| JP | 4-323847 | 11/1992 |
| JP | 11-223636 | 8/1999 |
| JP | 2001-26321 | 1/2001 |
| JP | 2005-249648 | 9/2005 |
| JP | 2005-300200 | 10/2005 |

* cited by examiner

*Primary Examiner* — James R Bidwell
(74) *Attorney, Agent, or Firm* — Oblon, Spivak, McClelland, Maier & Neustadt, L.L.P.

(57) ABSTRACT

A shuttle-type conveying system to convey an article. The system includes a feeding and collecting device capable of setting a cassette in which articles to be conveyed are stacked as they are on a rotating and feeding table, a pickup device taking out the article and placing it on a receiving/delivery table, and a conveying device feeding the article on the receiving/delivery table to another receiving/delivery table by a shuttle conveying portion traveling on conveying paths below the receiving/delivery table. After the article is lifted up by the shuttle conveying portion and moved to outside the receiving/delivery table, the article is lowered below the receiving/delivery table and made to travel under the receiving/delivery table to another receiving/delivery table.

2 Claims, 20 Drawing Sheets

FIG. 16
(a)
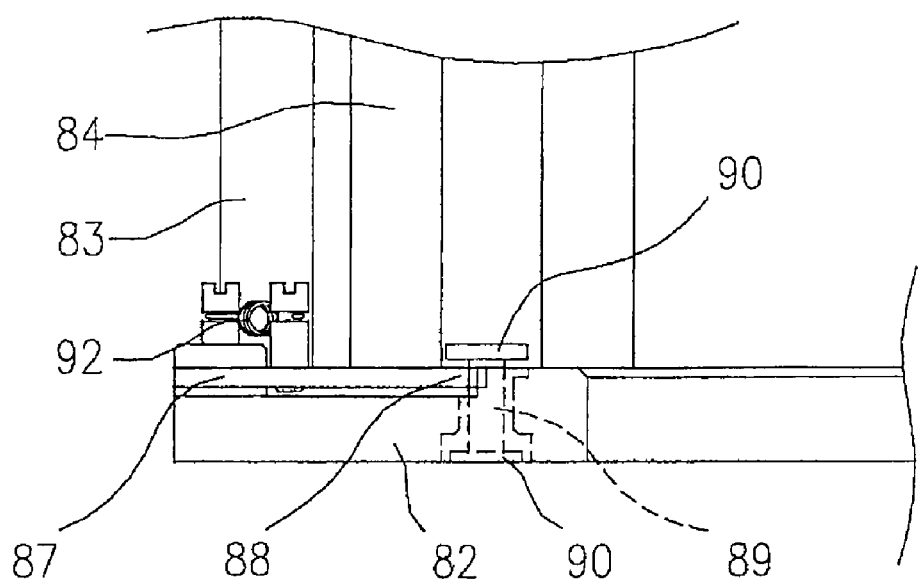
(b)
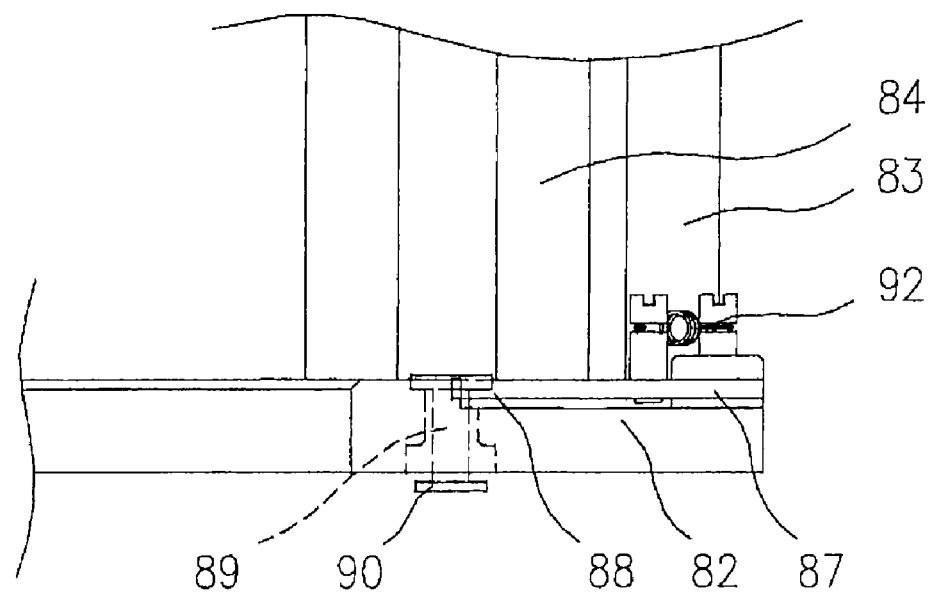

SHUTTLE TYPE CONVEYING DEVICE, MICROPLATE FEEDING AND COLLECTING DEVICE, PICKUP DEVICE FOR MICROPLATE, CASSETTE FOR MICROPLATE, AND SHELF FOR CONTAINING MICROPLATE

TECHNICAL FIELD

The present invention relates to a shuttle-type conveying device for conveying articles such as microplates used in a processing device for carrying out predetermined chemical reaction inspection, analysis and the like using a microplate, a microplate feeding and collecting device, a microplate pickup device, a cassette for microplate, and a shelf for containing microplate. In this description, the "shuttle-type conveying device" refers to a conveying device provided with a transfer portion (shuttle conveying portion) for conveying articles by reciprocating or circulating a single conveying path, or a closed conveying path (shuttle-type conveying path) such as an annular conveying path for example. The conveying device provided with a plurality of shuttle-type conveying paths are also included in a range of the shuttle-type conveying device of the present invention.

BACKGROUND ART

In the drug-discovery screening field, biotechnology field and the like, various tests such as biochemical reaction test of a substance are conducted. In these tests, as a container for containing a chemical or a sample for culture and biochemical reaction, a microplate provided with a plurality of hole-shaped wells in a single plate is used. Also, since these tests are conducted systematically with a large number of specimens as a target, a large number of microplates are usually used for processing such as dispensing operation and componential analysis. The present invention relates to a handling device of various microplates for efficiently containing, taking out, and conveying to a targeted position the microplate in a processing device using the microplate for these tests such as an assay processing device and the like, for example.

The "assay processing" here refers to detection and quantification of those generated or consumed by mixing compositions required for a chemical reaction in a test tube and the like and having them reacted under a certain condition. Such assay processing was manually conducted for each sample at the initial stage but in order to process a large number of samples at a high speed, a high-speed processing device which automates the processing has been developed in recent years.

As a prior art of such a device handling microplates, a microplate processing device in which the microplates are individually contained in a storage shelf on which a plurality of microplates can be placed, taken out one by one by a ceiling-traveling robot-type plate conveying mechanism as necessary and transferred to a dispensing stage and the microplates after the dispensing operation are returned to the storage shelf is proposed (See Patent Document 1).

Also, since the art disclosed in Patent Document 1 has a problem that a lid of a microplate can not be efficiently attached/detached, another conveying art is proposed in order to solve the problem (See Patent Document 2). With the art in Patent Document 2, a conveyer type microplate conveying mechanism is used, and the microplate is placed on the conveyer for conveying. On an upstream side of the conveyer, a device for removing a lid is provided at a position higher than the conveyer, thereby the lid is removed. The microplate whose lid has been removed is fed to a predetermined dispensing position, the dispensing processing is carried out on the conveyer, after the dispensing processing is finished, the microplate is fed to further downstream and the lid having been fed previously is placed. After that, the microplate with lid is collected by a collecting portion.

Moreover, a feeding device for taking out the microplates with lid one by one from a containing portion for stacking a large number of microplates with lid for storage and conveying them is proposed (Patent Document 3). Patent Document 3 discloses a prior art in which after the microplates with lid are stacked and contained in a first stock portion, all the stacked and contained microplates are moved to a second stock portion provided below the first stock portion and after that, the stacked microplates are taken out one by one in order from the top.

Patent Document 1: Japanese Patent Laid-Open No. 11-223636

Patent Document 2: Japanese Patent Laid-Open No. 2005-300200

Patent Document 3: Japanese Patent Laid-Open No. 2005-249648

DISCLOSURE OF THE INVENTION

Problems to be Solved by the Invention

In such a device handling a microplate, in addition to the dispensing processing, various processing such as incubation processing, analysis processing and the like are conducted, and a large number of microplates are used in these processing. According to requests of the various processing, rapid and accurate conveying of the microplates are demanded. In order to respond to these requests, the above-mentioned prior arts have various problems.

For example, the art in Patent Document 1 has a problem, as being pointed out in Patent Document 2, that a mechanism for removing the lid becomes complicated. In addition, since a dispensing stage (dispensing table) is located in the middle of a conveying path, there is a fear that the microplates during the dispensing processing are contaminated by a ceiling-traveling robot. More specifically, if a microplate is to be fed to a processing device on a downstream side from the dispensing table, since the ceiling-traveling robot is moved over the microplate placed on the dispensing table with its lid removed, there is a fear that trash such as dusts and the like drops onto the microplate placed on the dispensing table with its lid open and mixes into a sample.

Also, with the art described in Patent Document 2, the microplate is placed on a conveyer for conveying and the microplate in the middle of conveying is stopped on the conveyer for the dispensing processing. Therefore, it is not possible to feed the microplate prior to the microplate previously placed on the conveyer by skipping it. Thus, another microplate can not be fed ahead of the dispensing table till the dispensing processing and the like is finished, and conveying of another microplate is influenced by a dispensing processing speed and a conveying throughput is extremely lowered.

Moreover, even in Patent Document 3, which is a device for stacking and containing the microplates for supply or collect microplates one by one to or from the conveying device, there are various problems. In this way, if the microplates can be stacked and contained and sequentially supplied one by one according to a request, there is an advantage of efficient storage as compared with a case of containing the microplates in a containing shelf. However, in the art disclosed in Patent Document 3, when the microplate is contained in the first stock portion for the first time, the microplate should be inserted from top of an opening at a high position, and a labor load of a containing work is large. Also, it is so configured that after the stacked microplates are moved from the first stock portion to the second stock portion, the microplates having been moved to the second stock portion are taken out in order from the top, and at least two stock portions of the first and second stock portions are required, which increases the size and complexity of the entire device.

Moreover, with the art described in Patent Document 3, when the microplate constituted by two units separated into a lid portion and a main body portion is lifted to be taken out, the microplate is simply sandwiched by two arms on its side faces to be lifted up, and there is a fear that the main body portion and the lid are removed and dropped at the lifting-up.

Moreover, in the prior arts, the microplate placed on the shelf needs to be taken out by being gripped from the side, and control to take out the microplate on the shelf by a robot is complicated.

The present invention was made in view of the above problems of the prior arts and has an object to provide a shuttle-type conveying device whose conveying throughput per conveying path is improved with a simple structure.

Another object of the present invention is to provide a microplate pickup device that can lift up and take out the microplate without separating the lid portion and the main body portion.

Still another object of the present invention is to provide a microplate feeding and collecting device that can contain and take out stacked microplates efficiently.

Still another object of the present invention is to provide a cassette for microplate that can stack and contain microplates and can be easily attached to the microplate feeding and collecting device.

Still another object of the present invention is to provide a microplate containing shelf that can be assembled with accuracy and take out microplates placed on the shelf by a robot more easily.

Means for Solving the Problems

A first mode of the shuttle-type conveying device according to the present invention comprises at least one conveying path, a shuttle conveying portion provided with a conveying table portion that can be elevated up and down for reciprocating or circulating on the conveying path with an article to be conveyed on the conveying table portion, a receiving/delivery table arranged above the conveying path and provided with a bottom-face opening portion larger than the conveying table portion and smaller than the article to be conveyed, and a control portion for controlling the shuttle conveying portion so that the article to be conveyed which is placed on the receiving/delivery table is taken out, conveyed and placed on the receiving/delivery table at a conveying destination by movement on the conveying path of the shuttle conveying portion and an elevating operation of the conveying table portion.

In this mode, the article to be conveyed such as a microplate and the like placed on any of the receiving/delivery tables provided in plural at the end or in the middle of the conveying path is conveyed by taking it out of one receiving/delivery table by the shuttle conveying portion and conveying it to another receiving/delivery table, for example. The shuttle conveying portion reciprocates on a single conveying path. It may circulate or reciprocate on a ring-state closed conveying path. The conveying path may be a single straight line, a curved shape or a branch line extending from a single main line. Such conveying paths may be also provided in plural. The shuttle conveying portion is provided at least one at each conveying path. The receiving/delivery table is preferably located immediately above the conveying path and capable of traveling between the conveying path and the receiving/delivery table in a state where the shuttle conveying portion has the article to be conveyed placed.

Another mode of the shuttle-type conveying device according to the present invention is characterized in that the control portion comprises a take-out control portion that moves the shuttle conveying portion to below the receiving/delivery table with the conveying table portion lowered and raises the conveying table portion from below the receiving/delivery table and has it passed through the bottom-face opening portion, thereby to lift up the article to be conveyed placed on the receiving/delivery table, a conveying control portion for moving the conveying table portion with the article to be conveyed to the receiving/delivery table to be a conveying destination, and a receiving/delivery control portion that moves the shuttle conveying portion with the article to be conveyed to above the bottom-face opening portion of the receiving/delivery table to be the conveying destination and then, lowers the conveying table portion so that the article to be conveyed is placed on the receiving/delivery table of the conveying destination.

In this mode, in order to receive the article to be conveyed, the shuttle conveying portion is moved to immediately below the receiving/delivery table and the article to be conveyed is taken out of the receiving/delivery table by raising the conveying table portion and lifting up the article to be conveyed from immediately below, and after the article to be conveyed is moved to immediately above the delivery table in a lifted-up state, the conveying table portion is lowered so that the article to be conveyed is taken out and delivered by the shuttle conveying portion at the receiving/delivery table.

Another mode of the shuttle-type conveying device according to the present invention is characterized in that after the article to be conveyed is lifted up by the receiving/delivery control portion, the conveying control portion moves the shuttle conveying portion to outside the receiving/delivery table and then, lowers the conveying table portion to a position lower than the receiving/delivery table, has the shuttle conveying portion with the article to be conveyed passed and moved below the receiving and delivery table and raises the receiving/delivery table in front of the receiving/delivery table to be a conveying destination.

In this mode, the shuttle conveying portion lifts up the article to be conveyed and takes it out of the receiving/delivery table and then, lowers the conveying table portion so that the shuttle conveying portion travels below the receiving/delivery table. As a result, even if the receiving/delivery table is located in the middle of the conveying path, the article to be conveyed can be conveyed to the receiving/delivery table ahead.

Another mode of the shuttle-type conveying device according to the present invention is characterized in that a work table is provided on the conveying path so as to bridge over the conveying path, and when the shuttle conveying portion passes and moves below the work table, the article to be conveyed is conveyed to the receiving/delivery tables provided on upstream and downstream sides of the conveying path with the work table between them.

In this mode, even if the work table for dispensing processing and the like is provided in the middle of the conveying path, the article to be conveyed can be conveyed over the work table.

A first mode of the pickup device for microcassette according to the present invention is a pickup device provided with a main body portion and a lid portion and for sandwiching and taking up a rectangular microplate whose main body portion and lid portion can be sandwiched, respectively, from the side faces, comprising a pair of sandwiching arms for bringing one sandwiching arm into contact with the main body portion and the other sandwiching arm with the lid portion so as to sandwich the microplate from right and left when the side face of the microplate is sandwiched and held, an opening/closing driving portion for opening/closing driving the pair of sandwiching arms, an elevation driving portion for elevating the pair of sandwiching arms vertically, and a pickup control portion for controlling operations of the opening/closing driving portion and the elevation driving portion.

In this mode, by individually sandwiching the lid portion and the main body portion of the microplate from right and left so as to press each other by the pair of sandwiching arms, the lid portion and the main body portion are not separated when the microplate is lifted up.

Another mode of the pickup device for microcassette according to the present invention is characterized in that the pair of sandwiching arms diagonally sandwich the main body portion and the lid portion at heights different between right and left.

In this mode, in order that each of the sandwiching arms surely grips the lid portion and the main body portion, the heights of microplate contact portions of the respective sandwiching arms are made different. Thereby, the lid portion and the main body portion are pressed to each other diagonally so that the microplate is sandwiched and lifted up.

Another mode of the pickup device for microcassette according to the present invention is further provided with a detection sensor for detecting a height position of the microplate to be sandwiched.

Another mode of the pickup device for microcassette according to the present invention is further provided with a pair of holding members for holding the bottom face of the microplate from side faces perpendicular to the pair of sandwiching members.

Another mode of the pickup device for microcassette according to the present invention is characterized in that the pickup control portion controls so that after the microplate is slightly lifted up by the pair of sandwiching portion, the bottom face of the microplate is held by the pair of holding members.

A first mode of the microplate feeding and collecting device according to the present invention comprises a single elevation portion provided with a lift member for lifting the stacked microplates from the bottom portion and a cassette containing table provided with an opening portion at a bottom face through which the lift member can pass and an opening portion at an upper face through which the microplate can pass and capable of attaching a cassette for stacking and containing the microplates.

Another mode of the microplate feeding and collecting device according to the present invention is characterized in that the cassette containing table can have a plurality of the cassettes placed.

Another mode of the microplate feeding and collecting device according to the present invention is characterized in that the elevation portion is configured to be arranged at a position inscribing the inside of the cassette containing table and by rotation of the cassette containing table, each of the attached cassettes is brought into contact with a front face of the elevation portion.

Another mode of the microplate feeding and collecting device according to the present invention is characterized in that the elevation member is provided at the center part of the cassette containing table.

A first mode of the cassette for microplate according to the present invention comprises a side-face support frame for supporting the side faces of the microplate from three directions, a bottom-face support frame portion provided with an opening portion smaller than the microplate, an upper-face support frame portion provided with an opening portion larger than the microplate, and a short door portion for supporting the microplate from the opened remaining one direction of the side-face support frame.

Another mode of the cassette for microplate according to the present invention is characterized in that the bottom-face support frame portion is provided with a door lock pin that is lowered by the gravity and is projected from the lower side when being lifted up for locking the door portion in a closed state and that releases the door lock by being lifted upward and an elastic member for urging the door in a closing direction.

Another mode of the cassette for microplate according to the present invention is characterized in that the side-face support frame is made of a plurality of support rods connecting the upper-face support frame portion and the bottom-face support frame portion.

A first mode of the shelf for containing microplate according to the present invention is a shelf provided with a top board and a bottom board for containing microplate with a given interval between the top board and the bottom board and is characterized in that a shelf stage is formed in which support columns having at least one projection at an intermediate portion and for connecting the top board and the bottom board are arranged with a predetermined interval so that the microplate is supported by the projection.

Another mode of the shelf for containing microplate according to the present invention is characterized in that the top board and the bottom board are in a fan shape made of an arc with a small radius inside and an arc with a large radius outside.

Another mode of the shelf for containing microplate according to the present invention is characterized in that a section of the support column and the projection both have a circular section.

Another mode of the shelf for containing microplate according to the present invention is characterized in that the top board and the bottom board are supported by the support column with a small diameter on the small arc side on the inside and by the support column with a large diameter on the large arc side on the outside.

Another mode of the shelf for containing microplate according to the present invention is characterized in that the projection portion has its radius of the sectional shape gradually enlarged as it goes downward.

EFFECT OF THE INVENTION

According to the shuttle-type conveying device of the present invention, by the shuttle conveying portion in which the receiving/delivery table on which the article to be conveyed is placed is arranged on the conveying path and provided with the conveying table portion capable of being elevated up and down, with a simple operation of elevating the conveying table portion up and down, the article to be conveyed placed on the receiving/delivery table can be lifted up and taken out and the article to be conveyed can be placed on the receiving/delivery table. Also, by controlling the shuttle conveying portion so that it passes below the receiving/delivery table, even if the article to be conveyed stays on the receiving/delivery table in the middle of the conveying path, the article to be conveyed can be conveyed to the receiving/delivery table ahead and the conveying throughput in the shuttle-type conveying path can be drastically improved.

By the micro cassette feeding and collecting device according to the present invention, a cassette that can stack and contain the microplates can be set as it is in the cassette containing portion. Also, in the cassette containing portion, a plurality of cassettes can be set, and since the cassette containing portion can be constructed so as to be rotatable, many microplates can be contained in a relatively small space efficiently. Also, since the cassette containing portion is located at a low position, even a heavy cassette can be easily set in the cassette containing portion, and a work load for the cassette can be drastically reduced.

In the pickup device according to the present invention, when the side faces of the microplate constituted by the lid portion and the main body portion is sandwiched and lifted up, the microplate is sandwiched so that one of the right and left two sandwiching arms is brought into contact with the lid portion and the other is in contact with the main body portion, and the microplate is lifted up in a state where the lid portion and the main body portion are pressed to each other. As a result, when the microplate is lifted up, separation between the lid portion and the main body portion can be prevented.

In the microcassette device of the present invention, the microplates are stacked and contained by the support frames in three directions and a small door on the entire face, an opening through which a lift piece can pass is provided on the bottom face and the entire face, and by providing the opening through which the entire microplate can pass on the upper face, the cassette can be directly set in the microcassette feeding and collecting device of the present invention. In this cassette, the entire face door can be opened so that the microplate can be easily stacked and contained. By using this cassette, containing and transportation work burdens of the microcassette can be drastically reduced.

BRIEF DESCRIPTION OF THE DRAWINGS

FIG. 16 is a partially enlarged side view illustrating a relation between a door lock pin and a stopper.

Figure 1:
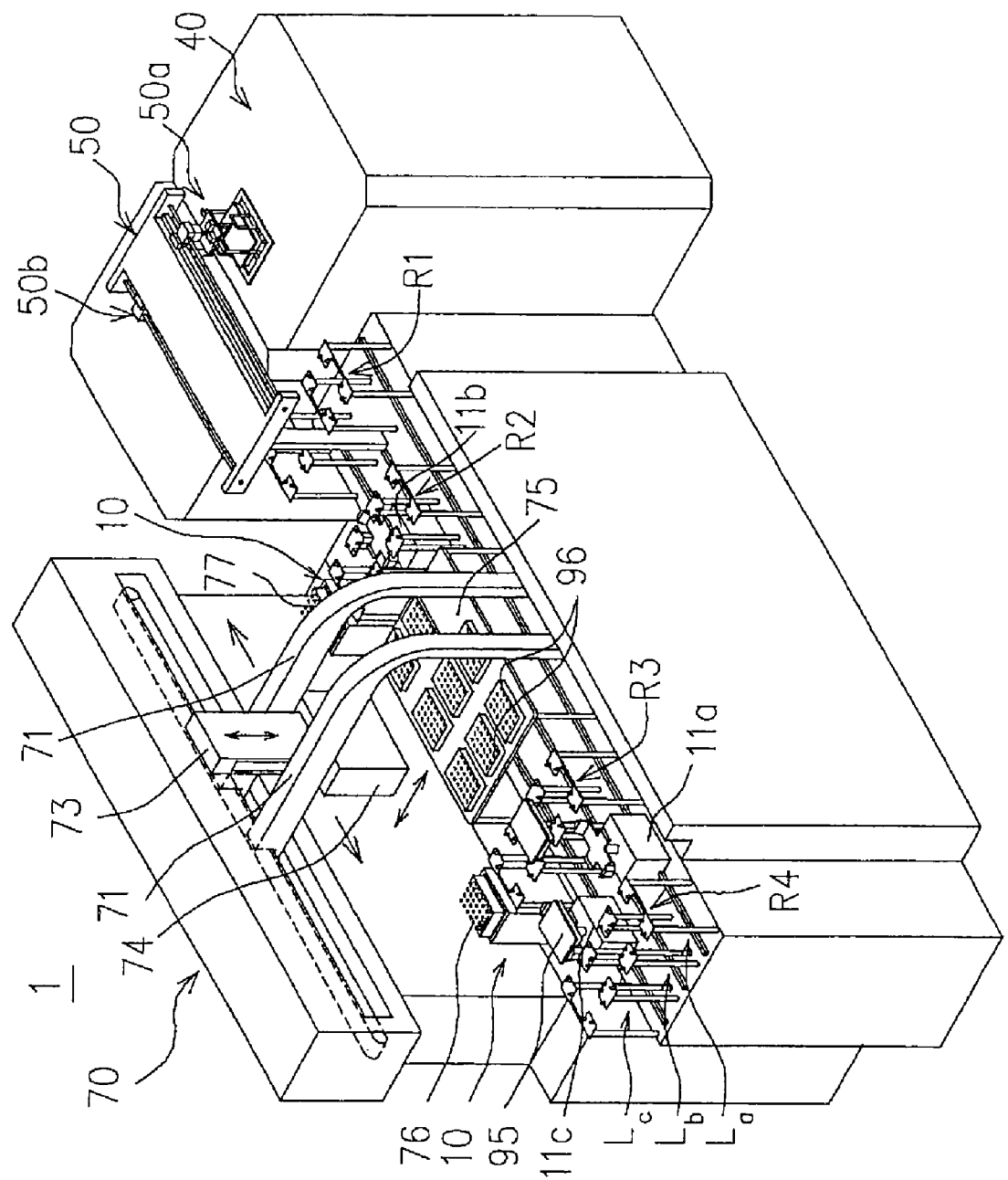
FIG. 1 is a perspective view illustrating an example of an analysis processing system using a shuttle-type conveying device and the like of the present invention.

EXPLANATION OF REFERENCE NUMERALS 1 analysis processing system
10 shuttle-type conveying device
11 shuttle conveying portion
12 conveying table portion
13 linear guide
14 gear
15 shuttle motor
16 roller
17 air cylinder
18 elevation rod
20 support portion
21 support plate
22 positioning pin
25 base table
27 timing belt
28 lid suction machine
29 belt fixing portion
30 rodless cylinder for elevation
40 microplate feeding and collecting device
41 containing portion frame
42 base portion
43 containing table
43a positioning pin
44 opening for lift piece
45 plate elevation portion
46 lift piece
50 pickup device
57 actuator for sandwiching
56 plate gripping portion
59 bifurcated round bar
60 plate-state plate
61 projection portion
62 actuator for holding
63 holding member
70 dispensing processing device
75 dispensing stage (dispensing table)

80 cassette for microplate
84 door
89 door lock pin
90 stopper
95 microplate
96 microplate main body portion
97 bottom face portion
98 lid portion
99 well
110 horizontally rotating-type conveying robot
120 containing shelf
121 thin support
122 thick support
123 top board
124 bottom board
130 analyzer
140 humidity retaining machine
La to Lc shuttle-type conveying path
R1 to R4 receiving/delivery table

BEST MODE FOR CARRYING OUT THE INVENTION

Figure 2:
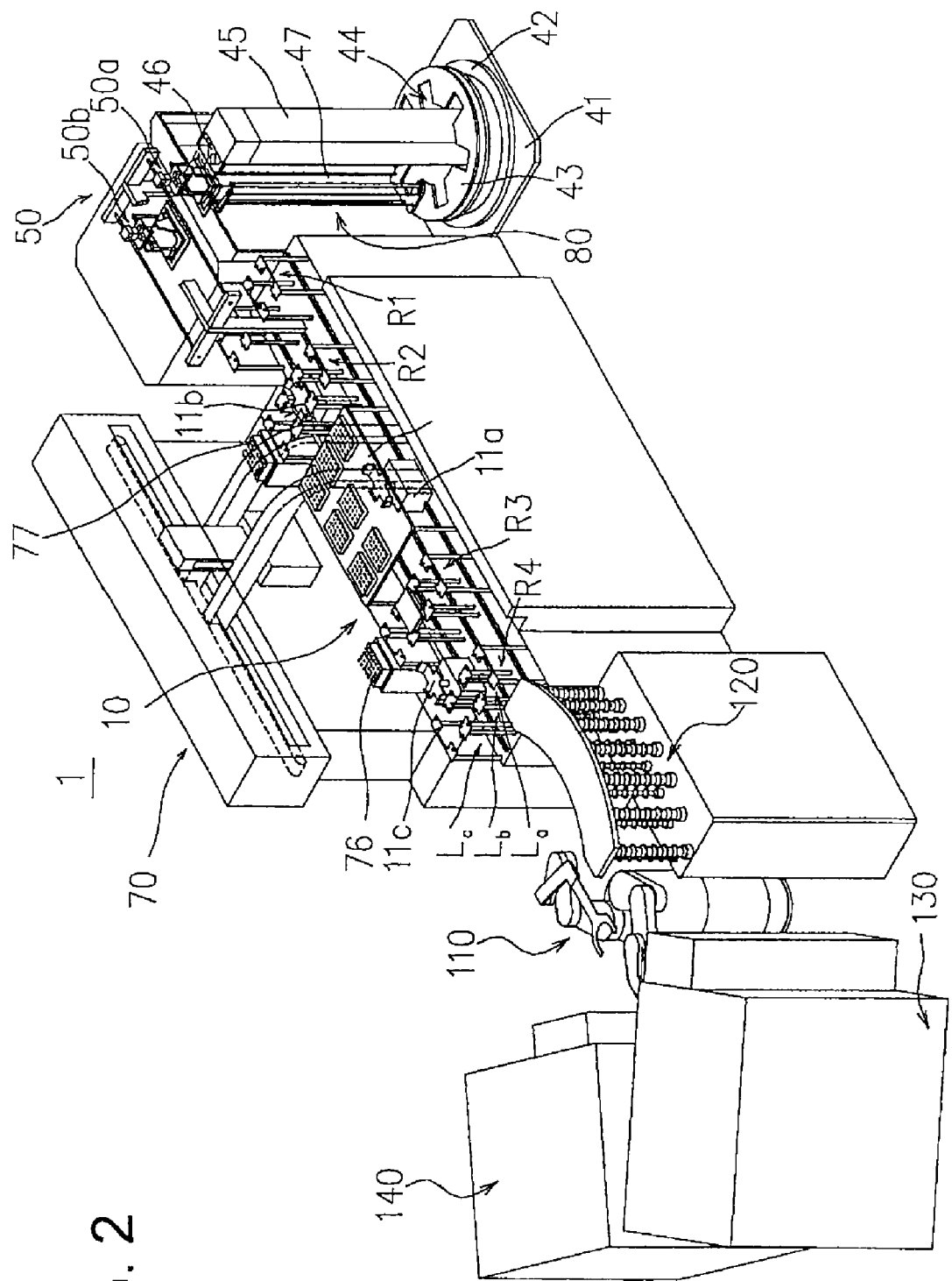
FIG. 2 is a partially cut-away view illustrating an inside of a feeding and collecting portion of the analysis processing device shown in FIG. 1.
Figure 3:
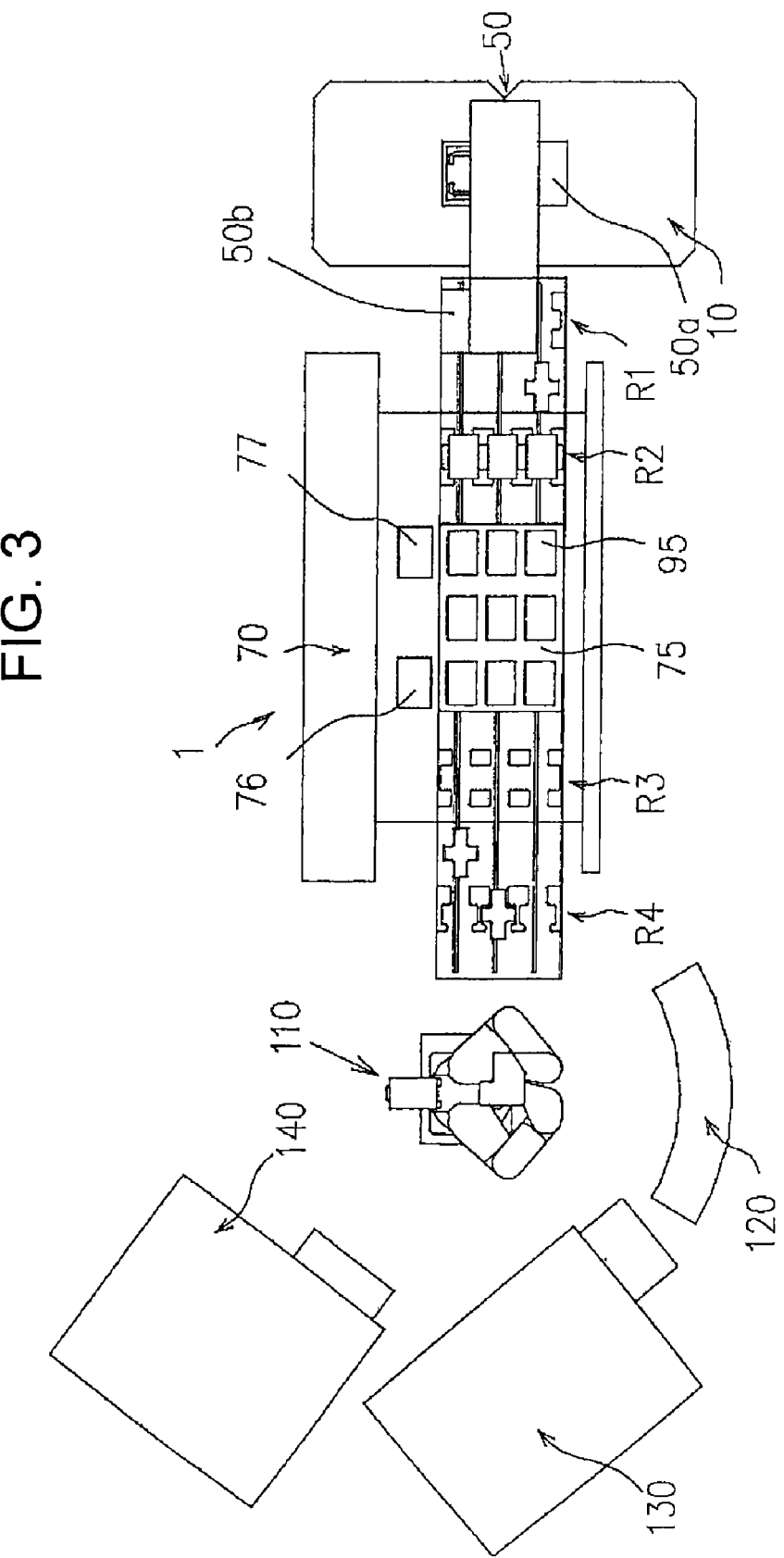
FIG. 3 is a plan view of the analysis processing device shown in FIG. 1.
Figure 4:
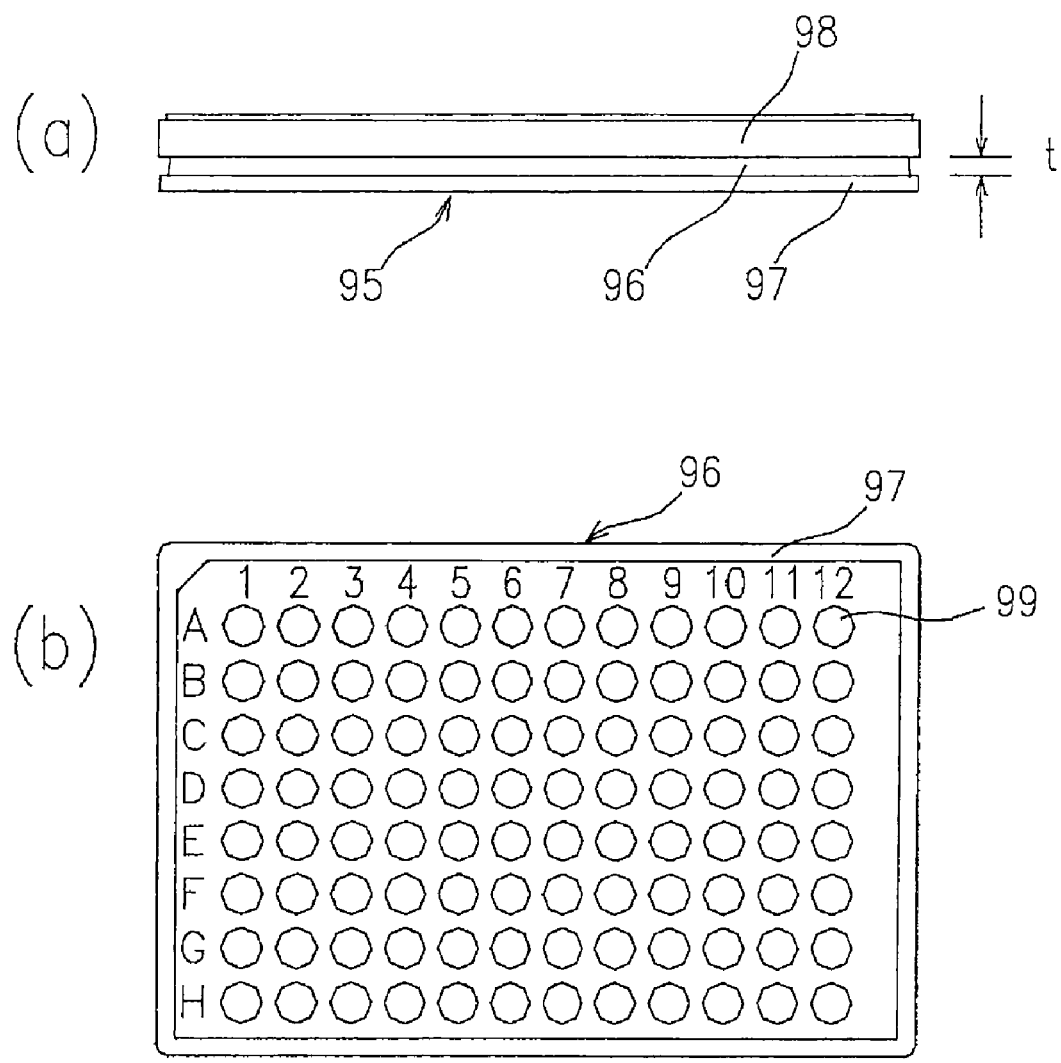
FIGS. 4 are side view and plan view illustrating an example of a microplate handled by the shuttle-type conveying device and the like according to the present invention.

FIG. 1 is a perspective view illustrating an example of an analysis processing system for carrying out processing such as drug-discovery screening field and the like using a shuttle-type conveying device and a microplate feeding device according to an embodiment of the present invention, and FIG. 2 is a perspective view illustrating an internal structure of a microplate feeding and collecting portion 40 of the system shown in FIG. 1 by partially cutting away its cover. FIG. 3 is a plan view of an analysis processing system 1 shown in FIGS. 1 and 2, and FIGS. 4 are side view and plan view illustrating an example of the microplate used in these devices.

[Structure of the Microplate]

First, using FIG. 4, a microplate 95 handled in the present invention will be described. The structure and size and the like of the microplate 95 are standardized to a certain size and shape. The analysis processing system 1 is, as mentioned above, a device for dripping and mixing processing of a test reagent in a sample for monitor, and the microplate used for this is provided with a large number of small well-state holes (wells) into which the sample can be injected so that the large number of samples can be inspected and analyzed at the same time. FIG. 4 shows an example of such a microplate and shows a box-shaped microplate of 85.5×127.8 mm made of plastic in which small hole-shaped containers arranged in 12 pieces laterally×8 pieces vertically, totaling in 96 pieces (hereinafter referred to as a "well 99") are provided. FIG. 4A is a side view of the microplate, FIG. 4B is a plan view of a state where the lid is removed, and as shown in FIG. 4A, the microplate 95 is constituted by a microplate main body portion 96 and a lid portion 98. The microplate main body portion 96 has a bottom face portion 97 with substantially the same width of the lid portion 98, whose peripheral edge slightly protrudes from the main body. A thickness "t" of the microplate 95 is different depending on the type of the microplate.

In the drug-discovery research field relating to development of synthetic drugs and biochemical drugs, several hundreds of thousands or several millions of samples are given High Throughput Screening. Therefore, other than the microplate 95 provided with 96 pieces of wells 93 as shown in FIG. 4, in order to handle much more samples, a microplate with the same outer dimensional size as that of FIG. 4 with 384 well or 1534 well provided are developed. In the analysis processing system, since these microplates are used in a large number at the same time, it is demanded that the microplates 95 are taken out of a containing device 40 one by one and conveyed to a target position at a high speed. After dispensing of samples or reagents into the well 99 by a dispensing processing device 70, these microplates 95 are either left on a shelf 120 for a given time or given incubation processing by a humidity retaining machine 140 and the like as necessary and then, analysis processing is applied by various analyzers 130 including a visible-ray absorption spectrum analyzer, fluorometric analyzer, chemical light emission analyzer, radioisotope scintillation counter and the like. Thus, in the analysis processing device, the microplate 95 is required to be delivered to a predetermined location such as the feeding and collecting device 40, the dispensing processing device 70, the shelf 120, various analyzers 130, the humidity retaining machine 140 and the like at a high speed.

[Entire Configuration of Analysis Processing System 1]

The analysis processing system 1 is provided with the feeding and collecting portion 40 for feeding the unused microplate 95 or the microplate 95 into which a sample has been dispensed and for collecting and containing the used microplate 95, a first pickup portion 50 for taking up the microplate 95 one by one and for moving it from the feeding and collecting portion 40 to a receiving/delivery table R1 of a conveying portion 10 or from the receiving/delivery table R1 to the feeding and containing portion 40, a conveying system 10 for conveying the microplate 95 placed on the receiving/delivery tables R1 to R4 to another receiving/delivery table one by one, the dispensing processing portion 70 for picking up the microplate 95 placed on the receiving/delivery table and placing it on a dispensing table and for dispensing a drug solution to the well 99, the shelf 120 on which the microplate is placed, the analyzer 130, the humidity retaining machine 140, and a horizontally rotating-type conveying robot 110 for taking up the microplate and transferring it among the receiving/delivery table R4, the shelf 120, and various devices 130, 140.

In the analysis processing system 1, how to convey the microplate 95 can be freely set according to the processing purpose. In the analysis processing system 1, for example, it is possible to take out the unused microplate 95 or the microplate 95 into which the sample has been dispensed from the feeding and collecting portion 40, for example, to convey it to a dispensing stage (dispensing table) 75 for dispensing processing and then, to carry out analysis processing after incubation processing and the like or to return it to the collecting and processing device soon after the dispensing processing. By programming a procedure to convey the microplate in the control portion in advance according to a processing mode, the microplate can be conveyed in a predetermined order according to the processing.

[Shuttle-type Conveying Device]

The shuttle-type conveying device 10 for conveying the microplate 95 from one receiving/delivery table to another receiving/delivery table will be described. The shuttle-type conveying device 10 is, as shown in FIGS. 1 to 3, provided with a shuttle conveying portion 11 that moves on conveying paths La to Lb and conveying paths L1 to L3 and receiving/delivery tables R1 to R4. In addition, three reciprocating shuttle-type conveying devices are shown in FIGS. 1 to 3.

Figure 5:
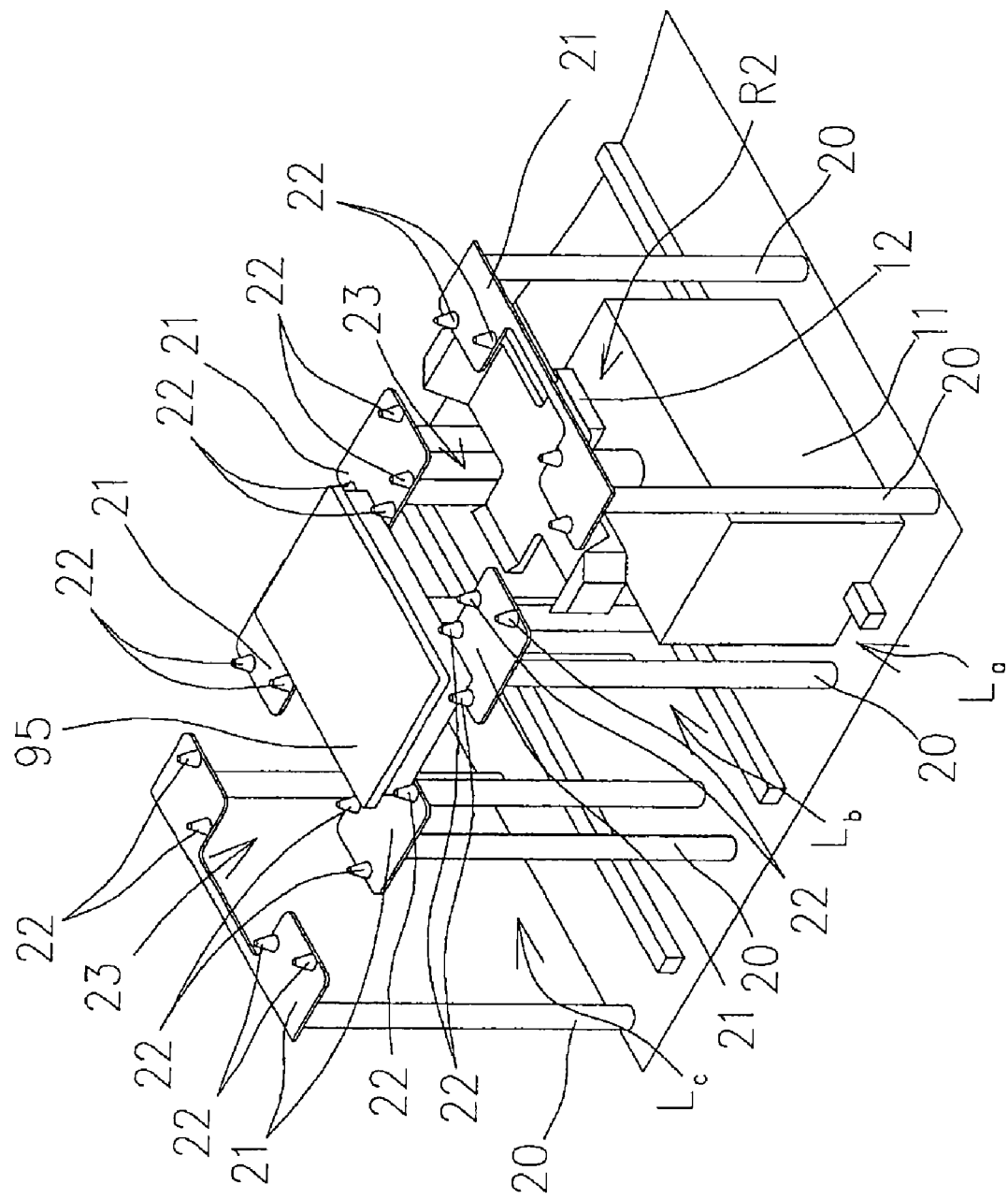
FIG. 5 is a perspective view showing a receiving/delivery table and a shuttle conveying portion of the shuttle-type conveying device shown in FIG. 1 in an enlarged manner.

A perspective view enlarging the receiving/delivery table R1 of the shuttle-type conveying device 10 and the shuttle conveying portion 11 shown in FIG. 1 is shown in FIG. 5. The receiving/delivery table R1 is provided on the conveying path, and the shuttle conveying portion 11 can pass and move under the receiving/delivery table R1. The shuttle conveying portion 11 is provided with a conveying table portion 12 capable of vertical elevation, and at a raised position, the conveying table portion 12 can be lifted up so that the conveying table portion 12 is higher than the receiving/delivery table R1. On the receiving/delivery table R1 in this embodiment, three microplates 95 in total can be placed for each conveying path L1.

The receiving/delivery table R1 is constituted by a small support plate 21 for supporting four corners of the microplate 95. The four support plates 21 support a single microplate 95. At the support plate 21, a plurality of elongated conical positioning pins 22 are provided for accurately positioning the microplate 95 at a predetermined position. Since the positioning pin 22 is formed in a conical shape, the microplate 95 is lowered along a diagonal peripheral wall of the positioning pin when the microplate 95 is placed and accurately positioned and held.

The support plate 21 is supported by a support column portion 20 so that it slightly protrudes to the conveying paths La to Lc side. In this way, since the receiving/delivery table R2 is constituted by the small support plates 21 supporting the four corners, an opening 23 is formed on an upper part of each of the conveying paths La to Lc of the receiving/delivery table R2, and the conveying table portion 12 of the shuttle conveying portion 11 can extend through the opening 23 from immediately below the receiving/delivery table R2 to over the receiving/delivery table R2. Therefore, when the microplate 95 is placed as in the conveying path Lb, by raising the conveying table portion 12 of the shuttle conveying portion from immediately below Lb, the microplate 95 can be lifted up over the receiving/delivery table R2. The shuttle conveying portion 11 can move along the conveying path with the microplate 95 lifted up in this way and lifts up and takes the microplate 95 out of the receiving/delivery table R2.

When the microplate 95 is to be placed on the receiving/delivery table, the shuttle conveying portion 11 is moved to the center part of the receiving/delivery table in a state where the conveying table portion 12 with the microplate 95 is extended upward and then, the conveying table portion 12 is lowered to a lower side of the receiving/delivery table. Thereby, the conveying table portion 12 is lowered to below the receiving/delivery table through the bottom-face opening portion 23, but since the microplate is supported by the support plates 21 at the four corners, the microplate can be placed on the receiving/delivery table. This point will be described later.

Moreover, the support column portions 20 provided at both sides of the conveying paths La to Lb are arranged with an interval so that the shuttle conveying portion 11 can pass between the support column portions 20 with the microplate 95 supported. Therefore, the shuttle conveying portion 11 can pass and move under the receiving/delivery tables R1 to R4 with the microplate 95 placed on the conveying table portion.

As a result, on whichever of the receiving/delivery tables R1 to R4 the microplate 95 is placed, the shuttle conveying portion 11 can freely convey the microplate 95 by moving under the receiving/delivery tables R1 to R4.

Figure 6:
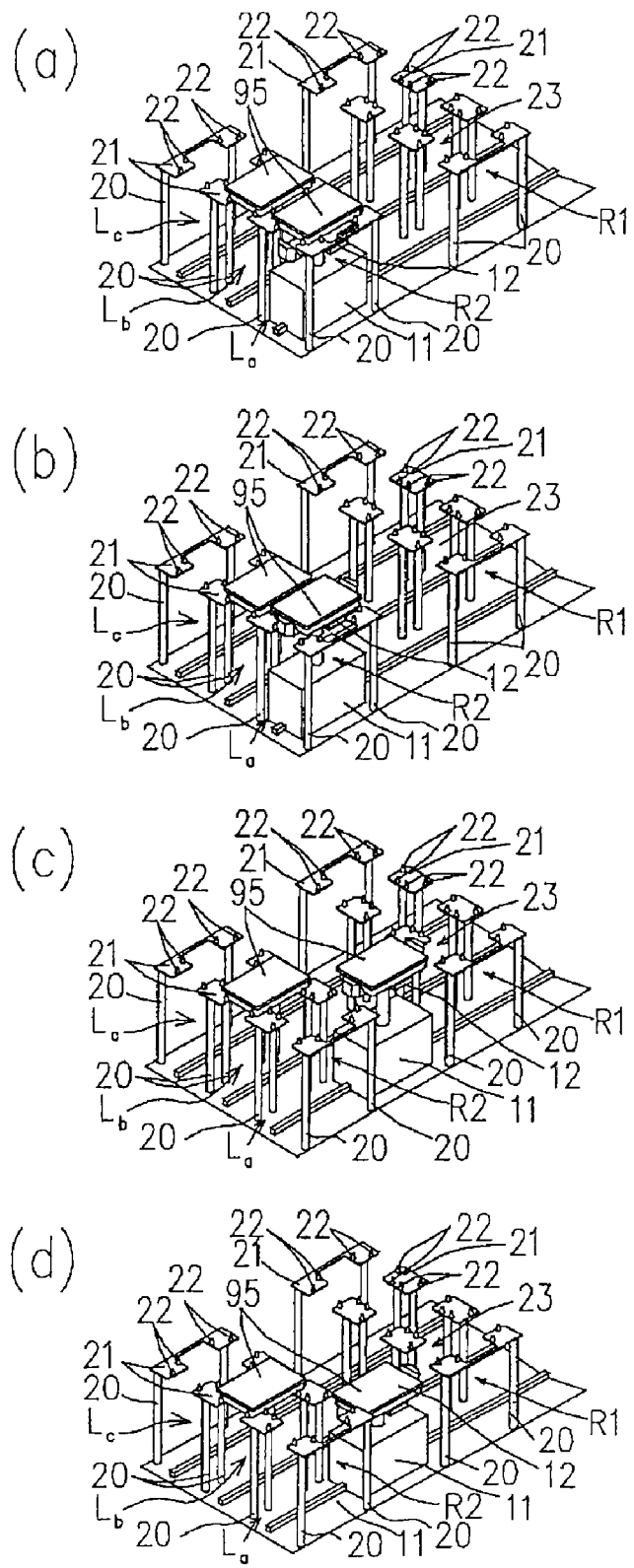
FIG. 6 is a perspective view illustrating a processing procedure from lifting up and taking out the microplate placed on the receiving/delivery table and to lowering it to a position lower than the receiving/delivery table.

FIG. 6 shows a processing procedure that the microplate 95 placed on the receiving/delivery table R4 is lifted up and taken out and lowered to a position below the receiving/delivery tables R4 to R1. First, as shown in FIG. 6A, the shuttle conveying portion 11 is moved to below the receiving/delivery table R4. Then, an air cylinder 17 is driven so as to raise the conveying table portion 12 and to lift up the microplate 12 (FIG. 6B). In that state, the portion is moved to between the deliver tables R4 and R3 (FIG. 6C), and the conveying table portion 12 is lowered so as to hold the microplate 95 at a position lower than the receiving/delivery tables R3, R4. As a result, since it can freely move under the receiving/delivery tables R1 to R4 and the dispensing table 75 for conveying, the microplate 95 can be conveyed to any position on the conveying path La.

Figure 7:
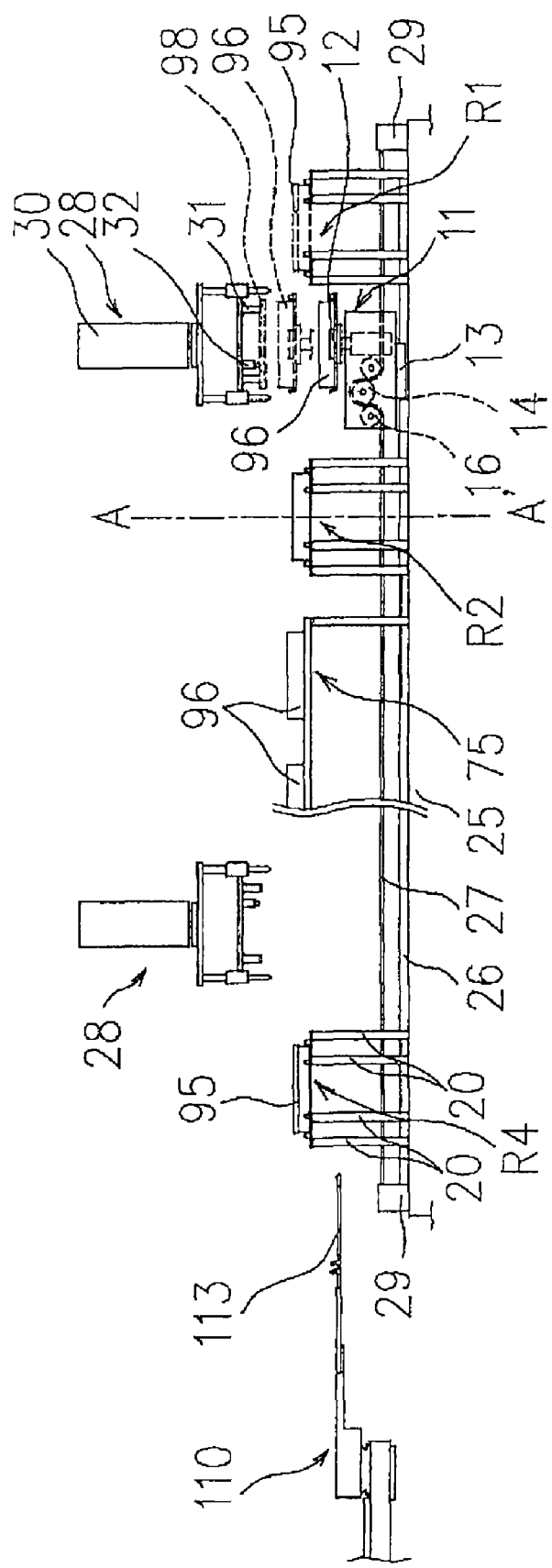
FIG. 7 is a partially omitted side view of a shuttle-type conveying device 10.
Figure 8:
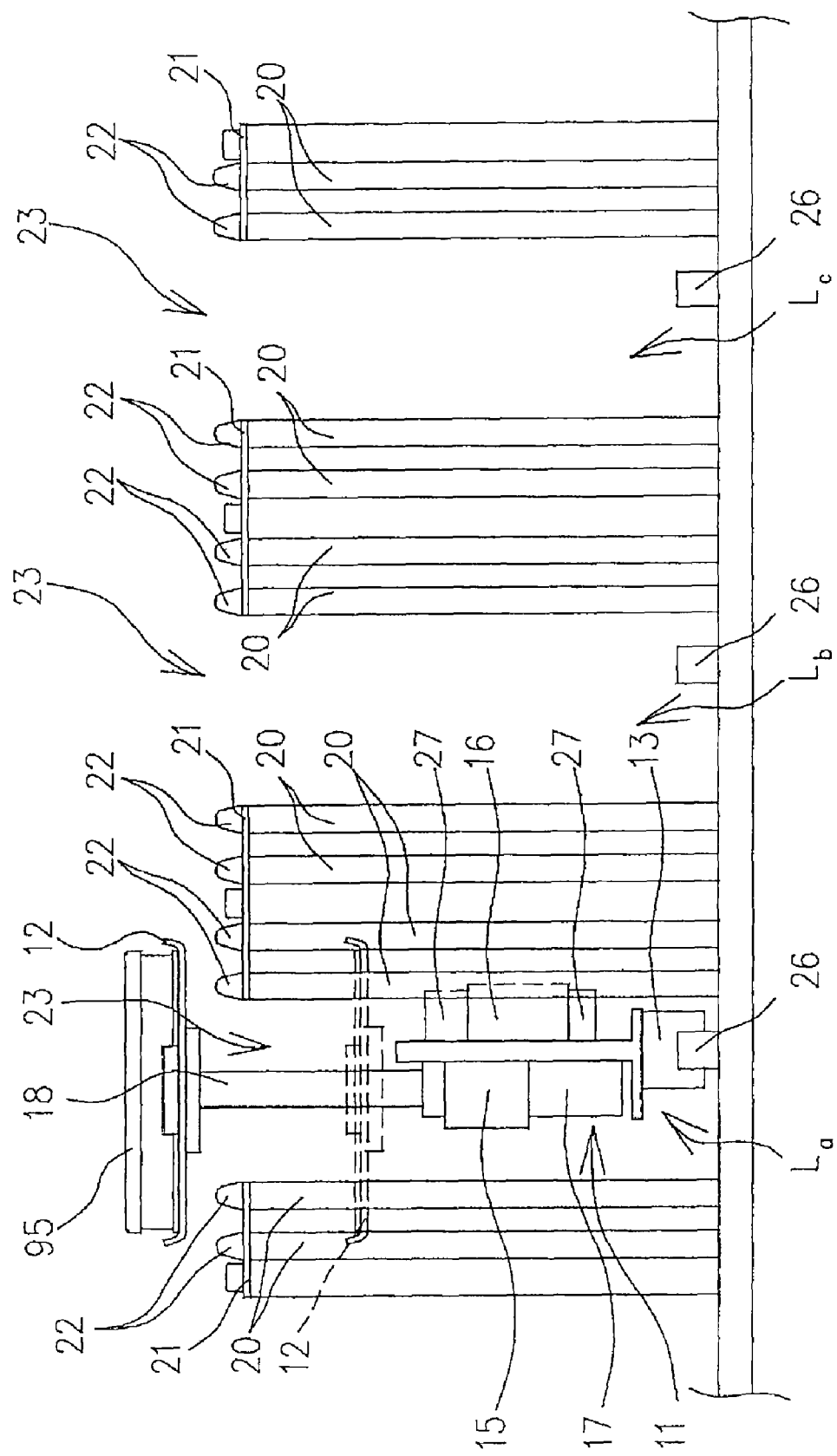
FIG. 8 is a view of the shuttle-type conveying device 10 seen from A-A' line direction in FIG. 7.

Using FIGS. 7 and 8, a conveying processing procedure to take the microplate 95 out of the receiving/delivery table and conveying it will be described. FIG. 7 is a partially omitted side view of the shuttle-type conveying device 10. FIG. 8 is a view of the shuttle-type conveying device 10 seen from A-A' line in FIG. 7. As for the conveying paths La to Lc, a linear guide rail 26 is laid on a base table 25, on which a linear guide 13 of the shuttle conveying portion 11 is slidably mounted. The linear guide 13 is provided with a shuttle motor 15 (See FIG. 8) on which a gear 14 is mounted, two rollers 16, and the air cylinder 17 provided upward. The air cylinder 17 vertically drives an elevation rod 18. At an upper end of the elevation rod 18, the conveying table portion 12 is fixed, and the conveying table portion 12 is elevated according to a vertical movement of the elevation rod 18.

Between the gear 14 and the two rollers 16, a straight timing belt 27 is fitted, and both ends of the timing belt 27 are fixed to a belt fixing portion 29 provided at both ends of the base table 25. The timing belt 27 has a smooth surface and has a waveform formed on a back face, and since it is meshed with the gear 14, when the shuttle motor 15 is rotated, the shuttle conveying portion 11 travels along the conveying paths La to Lc according to the rotation of the gear 14. As the shuttle motor 15 for self-traveling, a stepping motor is preferably used, and its rotation is preferably controlled accurately by a pulse signal. By controlling the rotation of the shuttle motor 15, the shuttle conveying portion 11 can freely move to and stop at a target position.

A procedure to take the microplate 95 out of the receiving/delivery table R1 and to open the lid portion 98 and to convey it by the shuttle conveying portion 11 will be described. When the microplate 95 on the receiving/delivery table R1 is taken out by the shuttle conveying portion 11, as shown in FIG. 8, the shuttle conveying portion 11 moves to immediately below the receiving/delivery table R1. In this state, as shown by a waved line in FIG. 8, the conveying table portion 12 is located below the receiving/delivery table R1. After that, as shown by a solid line in FIG. 8, the conveying table portion 12 is lifted up by driving the air cylinder 17. As a result, the microplate 95 is lifted up to a position higher than the positioning pin 22 of the receiving/delivery table R1. In this state, the shuttle conveying portion 11 is slightly moved to the left direction in FIG. 7 so as to take the microplate 95 out of the receiving/delivery table R1 and stops below a lid suction machine 28. In order to ease understanding of the structure of the shuttle-type conveying device 10, the lid suction machine 28 is not described in FIGS. 1 to 3.

The lid suction machine 28 is provided with a plurality of suction pads 31 and confirmation sensors 32 provided at a rodless cylinder 30 for elevation mounted. When the suction pad 31 is lowered by the rodless cylinder 30 for elevation and the lid portion 98 of the microplate is suctioned, a degree of pressure reduction is changed and suctioning is detected. By raising the suction pad 31 in this state, the lid portion 98 is lifted up and the lid is opened. The confirmation sensor 32 detects if the lid has been accurately closed or not from the position of the lid portion. Mounting of the confirmation sensor 32 is arbitrary.

If the microplate main body 96 with the lid portion 98 removed is to be placed on the receiving/delivery table R2, the shuttle conveying portion 11 is moved to the center of the receiving/delivery table R2 as it is, and by lowering the conveying table portion 12, the microplate main body 96 is placed on the receiving/delivery table R2. When the microplate main body 96 is to be conveyed to another receiving/delivery table R3 or R4, after the lid portion 98 is suctioned by the lid suction machine 28 as shown in FIG. 7, the shuttle table portion 12 with the microplate main body 96 placed is lowered to below the receiving/delivery tables R1 to R4 and the dispensing table 75. After that, the shuttle conveying portion 11 is passed and conveyed under the receiving/delivery table and the like, conveying is made to a target position.

In the case of conveying from the receiving/delivery table R1 to the receiving/delivery table R4 without the dispensing processing, since there is no need to remove the lid portion 98, the conveying table portion 12 is lowered at the position of the lid suction device 28 without removing the lid portion 98, and the shuttle conveying portion 11 is passed under the receiving/delivery tables R2, R3 and the dispensing table 75 and moved to the front of the receiving/delivery table R4. After that, the conveying table portion 12 is raised to the height above the receiving/delivery table R4, and after it is moved to the center of the receiving/delivery table R4, the conveying table portion 12 is lowered, and the microplate 95 is placed on the receiving/delivery table R4. The microplate 95 placed on the receiving/delivery table R4 is scooped up by a distal end portion 112 of an arm 111 in the conveying robot 110 and transferred to the shelf 120 or the other processing devices 130, 140. The microplate 95 having been processed is supported by the distal end portion 112 of the arm 111 in the conveying robot 110, lowered from above to below the receiving/delivery table R4 and placed on the receiving/delivery table R4.

When the microplate main body 96 for which the dispensing processing has been finished is returned to the receiving/delivery table R2, the shuttle conveying portion lifts up the microplate main body 96 from immediately below the receiving/delivery table and moves to below the lid suction machine 28. In this state, the suction pad 31 holding the lid portion 98 is lowered, and the lid portion 98 is placed over the microplate main body 96.

Since the dispensing processing is conducted with the lid portion 98 removed, the lid suction machine 28 is provided in front of the receiving/delivery table R2 for the dispensing processing. The receiving/delivery table R4 is a receiving/delivery table of the microplate having been conveyed for the incubation processing and other processing and also a receiving/delivery table on which the microplate 95 to be applied with a predetermined processing and the microplate for which the predetermined processing has been finished is placed. The dispensing processing might be conducted after the predetermined processing such as incubation. In the embodiment described in this description, in order to reduce the conveying distance and to improve a buffer function to absorb delay in the dispensing processing as much as possible in such a case, the receiving/delivery table R3 is further provided. In FIG. 7, in order to reinforce a function to remove the lid portion 98, the lid suction machine 28 is also provided in the vicinity of the receiving/delivery table R3.

As is obvious from the above description, according to the present invention, only by the elevation operation of the shuttle conveying portion 11 and the moving operation of the conveying path, the microplate 95 can be taken out of the receiving/delivery tables R1 to R4 and conveyed and placed on the other receiving/delivery tables R1 to R4. Therefore, even if the dispensing processing is slowed and the microplate 95 is left on the receiving/delivery table R2 or R3, for example, the microplate 95 can be conveyed between the receiving/delivery table R1 and the receiving/delivery table R4.

That is, according to the conveying method of the present invention, by means of a simple conveying mechanism provided with the shuttle conveying portion provided with the conveying table portion capable of vertical elevation operation and the receiving/delivery table on an upper part of the conveying path, a delay in the processing by one processing device making a bottleneck and also delaying conveying of the microplate 95 to another processing device on the same conveying path can be prevented. In this way, by providing a plurality of receiving/delivery tables according to the present invention, even if the receiving/delivery table in the middle of the conveying path is full, the microplate can be conveyed to the receiving/delivery table ahead. Therefore, the throughput of the shuttle-type conveying processing can be drastically improved. Also, since the receiving/delivery table serves a function of a conveying buffer, by providing a plurality of the receiving/delivery tables according to the present invention, the conveying throughput of one conveying path can be further improved. Particularly in the present invention, a remarkable effect of drastic improvement of the conveying throughput can be obtained only with a simple structure in which the conveying table portion elevating vertically at the shuttle conveying portion is provided and only by providing the receiving/delivery table having a bottom-face opening portion above the conveying path.

Figure 9:
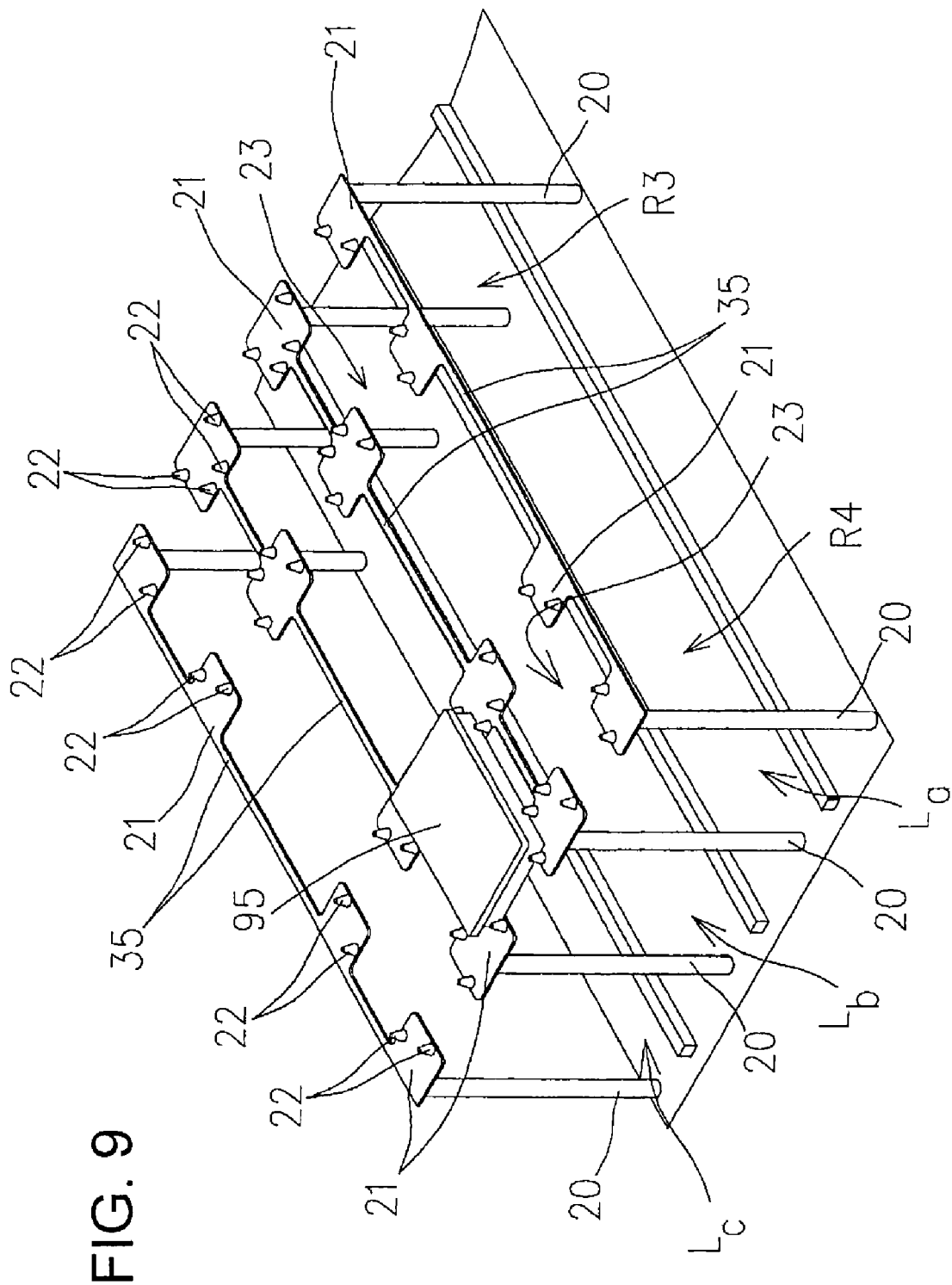
FIG. 9 is a perspective view illustrating another example for fixing s support plate of the receiving/delivery table.

In the above description, the structure in which the support plates 21 of the receiving/delivery tables R1 to R4 are supported by the support column portions 20 is shown, but as shown in FIG. 9, the support plate 20 may be fixedly provided on a support frame 35 laid at both ends of the conveying path at a predetermined height. At that time, by providing a plurality of screw holes by which the support plate 21 is mounted on the support frame 35 with a predetermined interval so that the support plate 21 can be mounted at an arbitrary position, installation positions and the number of installation of the receiving/delivery tables can be made easily changeable. Also, instead of the laid frame 35, a wall may be provided at a predetermined height so that the support plate 21 at its upper end is fixed.

Also, in the above-described embodiment, the example provided with three conveying paths La to Lc is shown, but the number of the conveying paths may be one or three or more.

[Microplate Feeding and Collecting Device]

Figure 10:
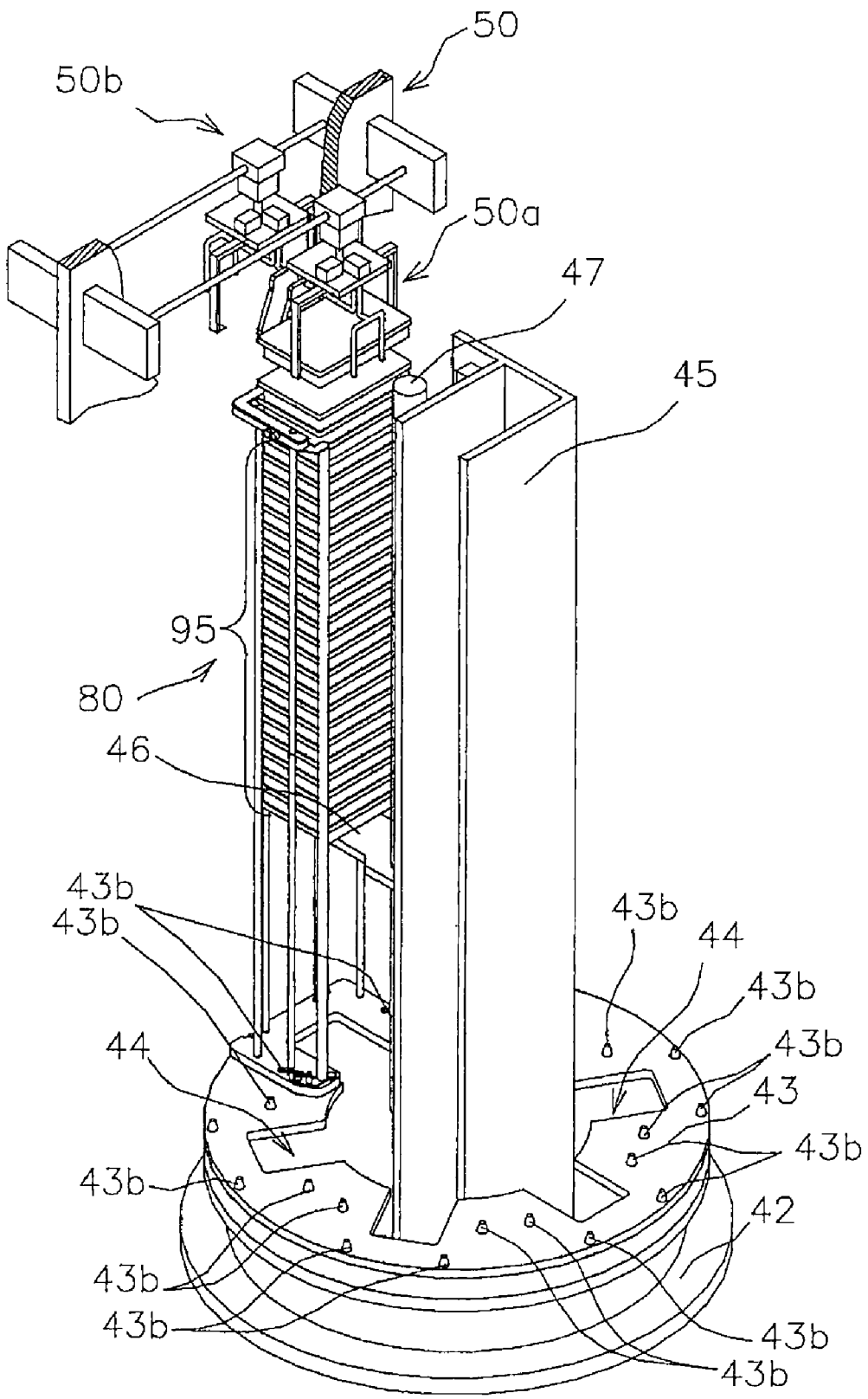
FIG. 10 is a partially cut-away perspective view illustrating a state where only one cassette in which a large number of microplates are stacked and contained is set in a rotating containing table.

Next, the microplate feeding and collecting device 40 will be described. FIG. 2 shows a part of an internal structure of the microplate feeding and collecting device 40. In FIG. 2, an example in which a microplate cassette 80 is set on a rotating and containing table (cassette containing portion) 43 is shown. The cassette 80 in FIG. 2 is shown such that most of the microplates 95 have been already supplied and the cassette 80 is almost empty. FIG. 10 is a partially cut-away perspective view showing a state in which only one cassette 80 in which a large number of microplates 95 are stacked and contained is set on the rotating and containing table 43. In FIG. 10, a state is shown that the microplate 95 on the uppermost stage is lifted up to a take-out position of the microplate 95 by a pickup device 50a.

Figure 11:
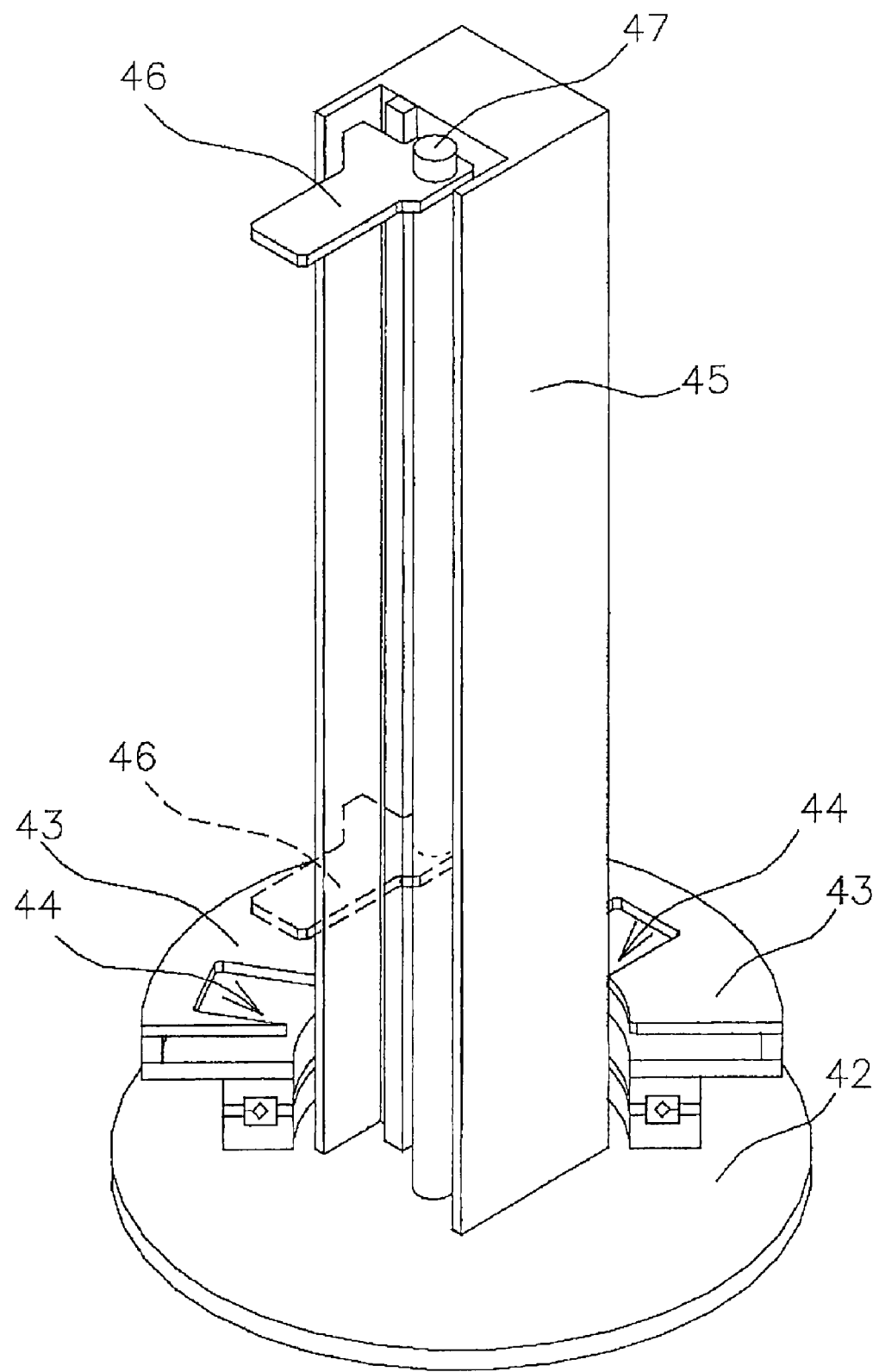
FIG. 11 is a perspective view of a state where the cassette is removed and the rotating containing table is cut away.
Figure 12:
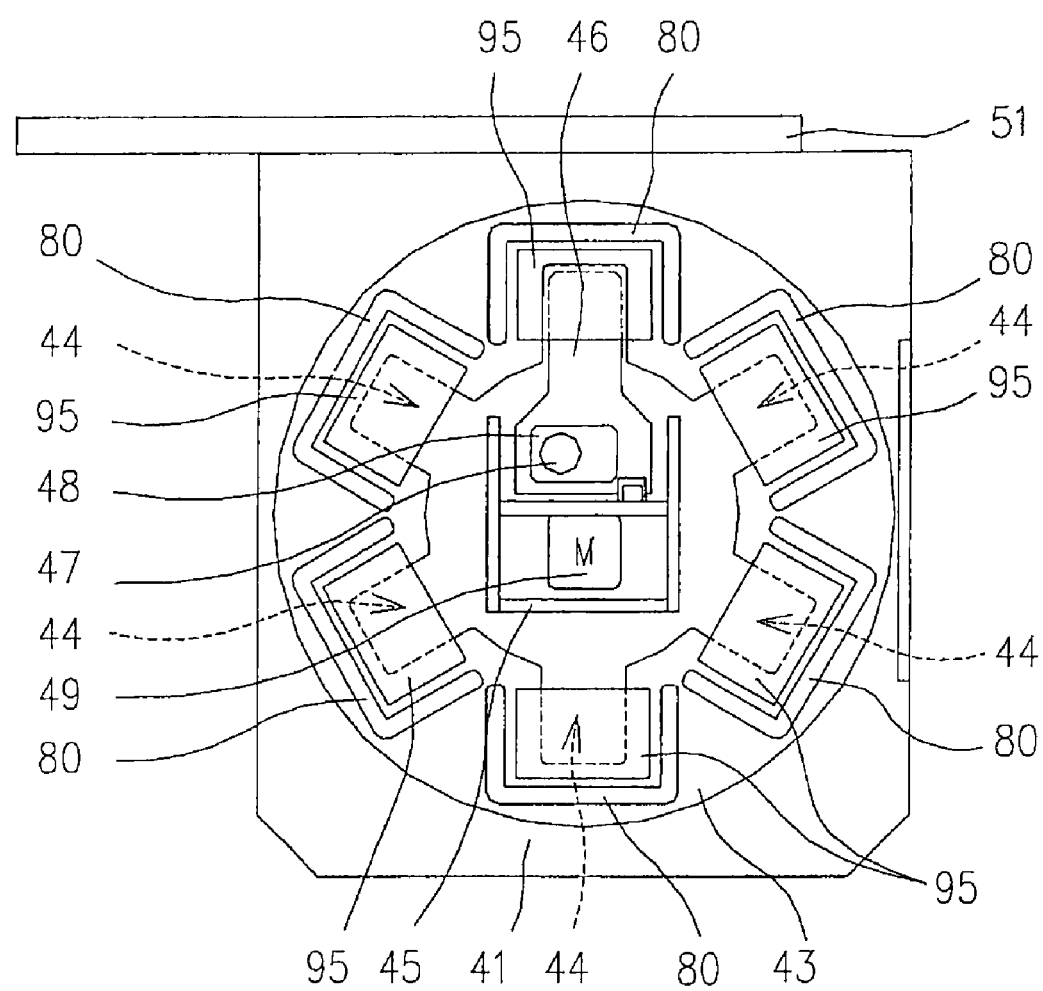
FIG. 12 is a schematic plan view of a state where six cassettes are set in the rotating containing portion.

On the rotating and containing table 43, 6 similar cassettes 80 can be set. But, FIGS. 3 and 10 show the state in which only one cassette is set. FIG. 11 shows a perspective view of a state where the cassette 80 is removed and the rotating and containing table 43 is cut away, and FIG. 12 shows a schematic plan view of a state in which 6 cassettes 80 are set on the rotating and containing portion 43. The rotating and containing table 43 is held on a base table portion 42 fixed to a frame 41 of the feeding and collecting portion 40 so that it can be rotated and driven by a rotary motor, not shown. At the center of the base table portion 42, a plate elevation portion 45 for lifting up the entire microplate stacked in the cassette 80 from below is fixed. The plate elevation portion 45 is provided with a lift piece 46 that can raise the entire microplate placed on it. The lift piece 46 is vertically driven by a ball screw 47 rotated and driven by a motor 49 for plate elevation portion (See FIG. 12).

As can be known from FIG. 10, the rotating and containing table 43 is provided with four positioning and fixing pins 43a at positions where the cassette 80 is set. In the rotating and containing table shown in FIG. 10, 6 cassettes can be set. The rotating and containing table 43 is provided with an opening (opening for lift piece) 44 at a position corresponding to the bottom face portion of the cassette 80, and when the rotating and containing table 43 is rotated, the lift piece 46 retreats through the opening 44 to below the rotating and containing table 43. After the rotating and containing table 43 is rotated and the cassette 80 in which the microplates to be taken out are stacked is stopped in front of the plate elevation portion 45, the lift piece 46 is raised through the opening 44 and pushes up the entire microplates stacked in the cassette 80 from the bottom face of the cassette 80, and the microplate 95 stacked on the uppermost stage is lifted up to a pickup position by the pickup device 50a as shown in FIG. 10.

The feeding and collecting portion 40 has the similar rotating and containing table 43 also provided on the side of a pickup device 5b, and 12 cassettes 80 in total can be contained. By setting the cassette 80 in which the microcassettes 95 are stacked, the microcassette 95 can be fed to the receiving/delivery table R1, and by setting the empty cassette 80 in the rotating and containing table 43, the microplate 95 having been collected from the receiving/delivery table R1 can be stacked and contained in the empty cassette 80 in the order of collecting. The plate elevation portion 45 is controlled to push up by one increment each time the microplate 95 is taken out in order from the above and is also controlled to lower by a portion of one microplate each time the microplate 95 is returned to the cassette 80. In this way, by moving the lift piece 46 vertically, the height of the microplate 95 on the uppermost stage in the cassette 80 is adjusted to the take-out position or return position by the pickup portion 50 all the time.

As can be known from the above description, in the microcassette feeding and colleting device of the present invention, the microplate can be set to the cassette containing portion as a cassette that can stack and contain the microplates. Also, since the plurality of cassettes can be set in the cassette containing portion and the cassette containing portion can be constructed so as to be rotatable, many microplates can be efficiently contained in a relatively small space. Also, since the cassette containing portion is located at a low position, even heavy cassettes can be easily set in the cassette containing portion, which can drastically reduce a work load of the cassette.

[Microplate Pickup Device]

Figure 13:
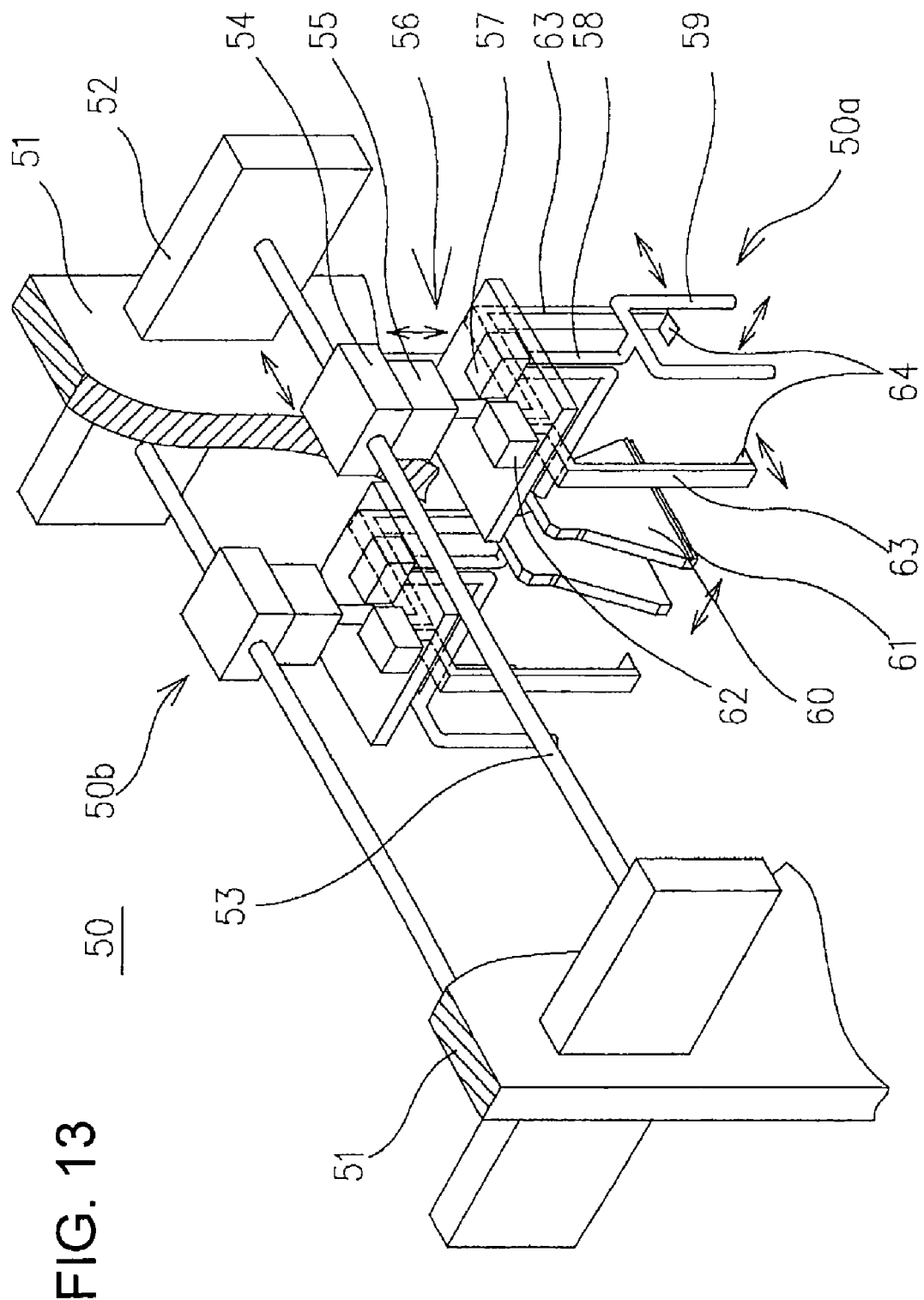
FIG. 13 is a partially cut-away perspective view illustrating an inside structure of a pickup device.
Figure 14:
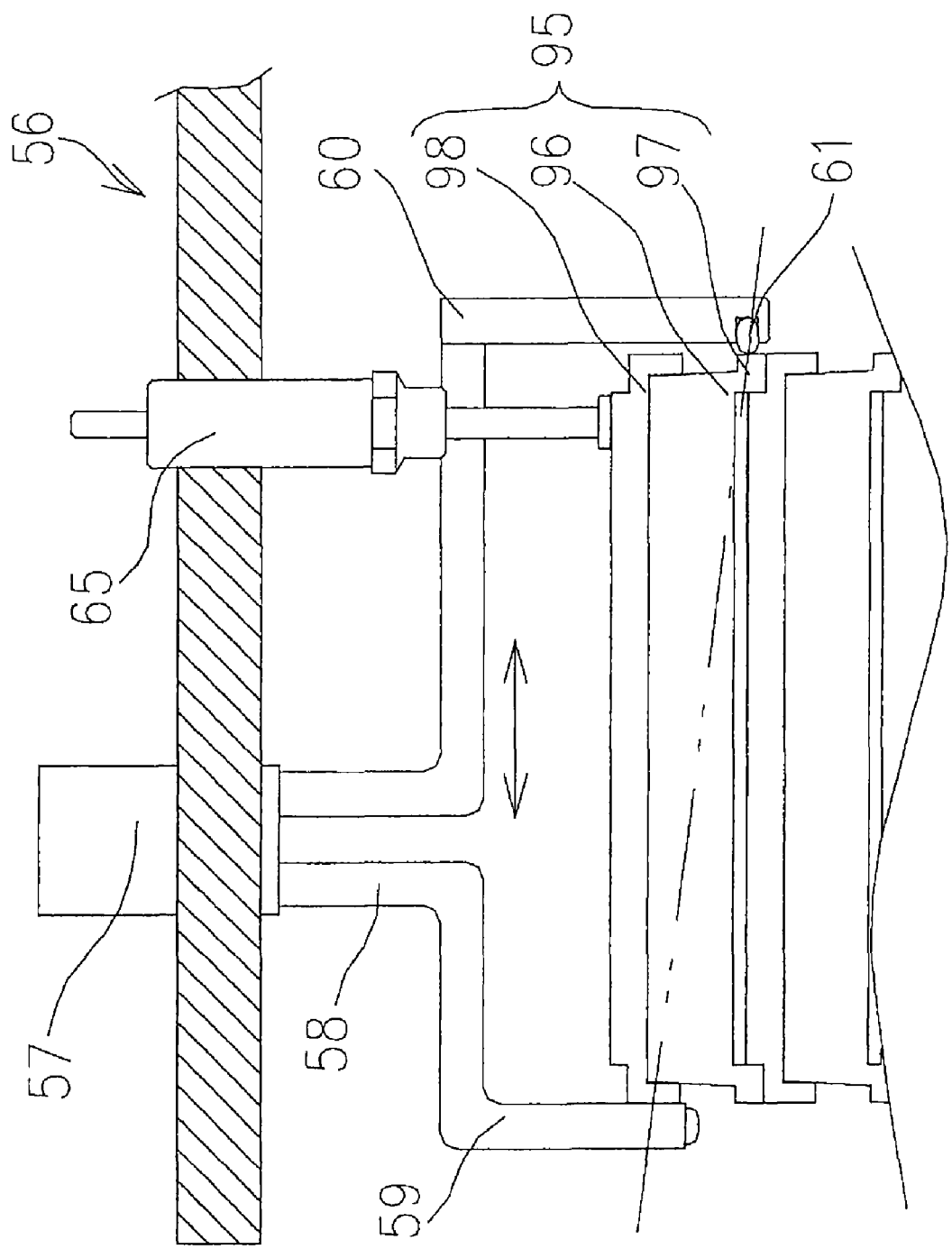
FIG. 14 is a side view schematically illustrating a sandwiching state of the microplate by the pickup device.

Next, the micro pickup device for taking up the microplate 95 from the feeding and collecting portion 40 and placing it on the receiving/delivery table R1 or for taking up the microplate 95 from the receiving/delivery table R1 and containing it in the cassette 80 of the feeding and collecting portion 40 will be described. An entire appearance of such a pickup device is shown as the first pickup device 50 in FIG. 1, and its internal mechanism is shown in FIG. 2. Using FIGS. 13 and 14, the internal structure and its function of the first pickup device 50 will be described in detail. FIG. 13 is a partially cut-away perspective view illustrating the internal structure of the first pickup device 50 and FIG. 14 is a side view schematically showing a sandwiched state of the microplate 95 by the first pickup device 50.

In this embodiment, two microplate pickup devices 50a, 50b for taking out the microplate 95 from the two rotating and containing tables 43, respectively, are provided. Since the microplate pickup devices 50a and 50b are identical, only the microplate 50a will be described below.

At both ends of the microplate pickup device 50, a cylinder support portion 52 mounted to a frame 51 is provided. On the cylinder support portion 52, a horizontal rodless air cylinder 53 is supported, to which an air cylinder movable portion 54 is mounted so as to be movable in the horizontal direction. At the air cylinder movable portion 54, an elevation rodless air cylinder 55 is mounted, to which a plate gripping portion 56 is mounted. Thereby, the plate gripping portion 56 can be elevated vertically and moved horizontally between the take-out position of the microplate 95 in the feeding and collecting device shown in FIG. 1 to the receiving/delivery table R1.

The plate gripping portion 56 is provided with a pair of sandwiching members constituted by a bifurcated round bar 59 and a plate-state plate 60 for sandwiching the both side faces of the microplate 95 and a pair of holding arms 63 for holding the microplate 95 by supporting its bottom face from the both side faces opposite to the pair of sandwiching members.

The plate-state plate 60 constituting the pair of sandwiching members is provided with a projection portion 61 at its bottom portion, in contact with the side face of the bottom-face projection portion 97 of the microplate main body portion. The projection portion 61 extends by a predetermined length in the side-face direction of the microplate 95. The plate-state plate 60 and the bifurcated round bar 59 can be moved by an actuator 57 for sandwiching, capable of being opened and closed, by which the microplate 95 is sandwiched by the projection portion 61 of the plate-state plate 60 and the distal end of the bifurcated round bar 59.

Using FIG. 14, the sandwiched state will be described. As mentioned above, the straight projection portion 61 is brought into contact with the bottom-face projection portion 97 of the microplate main body 96. On the other hand, the bifurcated round bar 59 has its distal-end position slightly higher so that its distal end is brought into contact with the side face of the lid portion 98 of the microplate 95. Thus, as shown in FIG. 14, when the microplate 95 is to be sandwiched by the distal end portion of the bifurcated round bar 59 and projection portion 61, since the lid portion 98 of the microplate and the microplate main body portion 96 are sandwiched so as to be diagonally pressed to each other, there is no separation between the lid portion 98 and the main body portion 96 when they are sandwiched and lifted up. In this way, in order to accurately sandwich the bottom face portion 97 of the microplate main body and the lid portion 98 diagonally, height adjustment of the plate gripping portion 56 is important, and thus, a height sensor 65 is provided so that the height of the plate gripping portion 56 is accurately adjusted by a plate detection signal from the height sensor.

When being slightly lifted up by being sandwiched by the pair of sandwiching members, then, the bottom face of the microplate 95 is held by the pair of holding arms 63. The pair of holding arms 63 can be moved capable of being opened/closed by the holding actuator 62. The pair of holding arms 63 are provided with claws 64 extending horizontally, respectively. The holding arms 63 are provided to be at a height where the claws 64 support the bottom face portion of the microplate when the microplate 93 is accurately sandwiched, and after the microplate 95 is slightly lifted up by the pair of sandwiching members, by closing the pair of holding members 63, the bottom face of the microplate 95 is surely held by the claws 64.

By the pair of sandwiching members and the pair of holding members 63, the plate gripping portion 56 gripping the microplate 95 is lifted up by the elevation rodless air cylinder 55. After that, it is moved by the horizontal rodless air cylinder 53 from the feeding and containing portion 40 to the receiving/delivery table R1 or from the receiving/delivery table R1 to the feeding and containing portion 40 horizontally. When it is moved to a predetermined position, the plate gripping portion 56 is lowered by the elevation rodless air cylinder 55 to a predetermined height and then, the pair of holding arms 63 and the pair of sandwiching members are released, and the microplate 95 is placed on the receiving/delivery table R1 or the uppermost stage of the cassette 40 in the feeding and containing portion 40.

[Cassette for Microplate]

Figure 15:
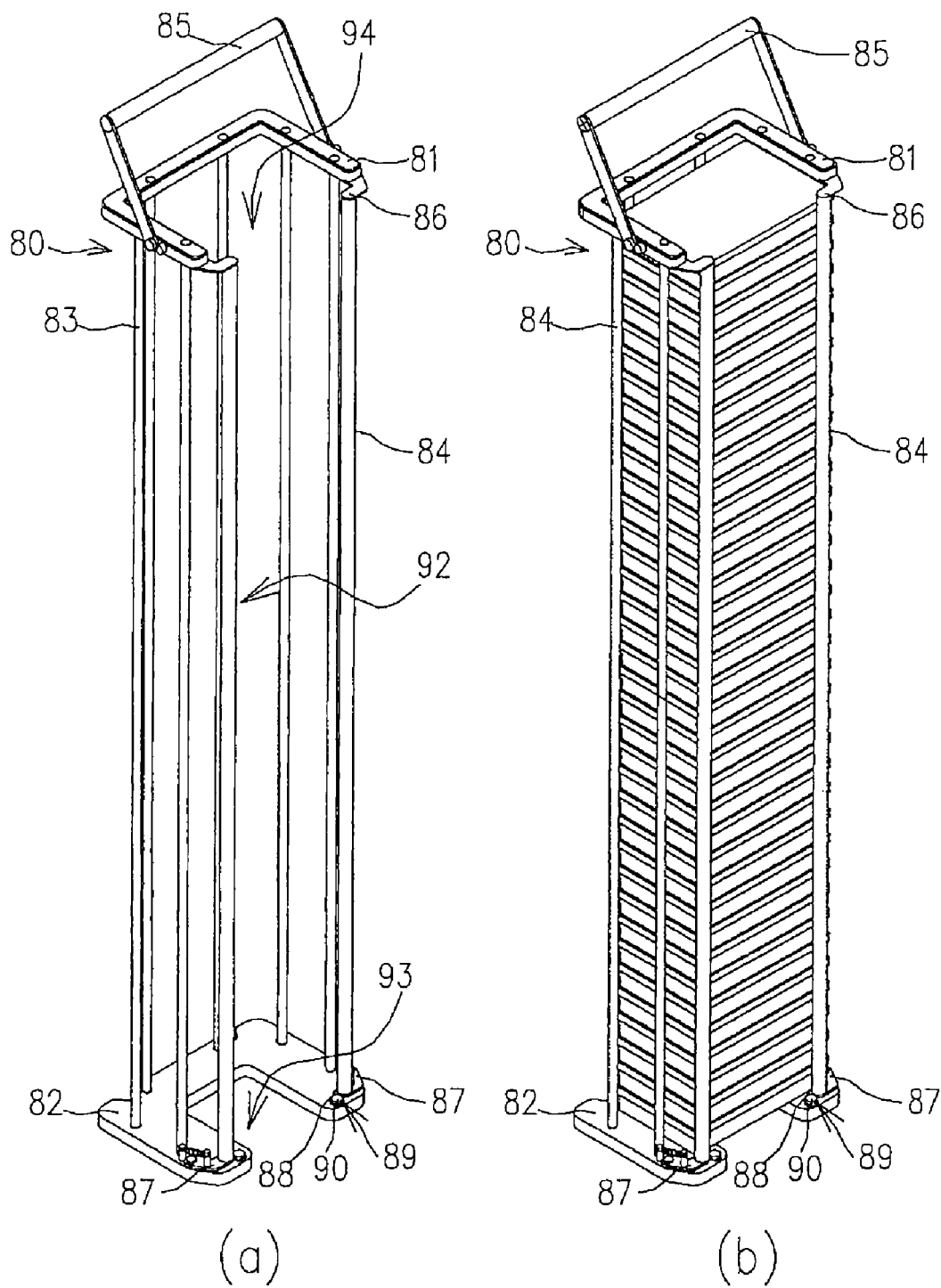
FIG. 15 is a perspective view illustrating an example of a cassette for microplate used in the microplate feeding and collecting device of the present invention.

An example of the cassette for microplate used in the microplate feeding and collecting device of the present invention will be shown in FIG. 15. FIG. 15A shows a state where the microplate 95 is not contained, while FIG. 15B shows a state where the microplate 95 is contained. The cassette 80 for microplate according to the present invention can stack and contain the microplates 95.

The cassette 80 fixes a cassette upper frame 81 and a cassette lower frame 82 made of only three sides of a substantial square by six metal pipes 83 arranged though them so as to connect the three sides of the upper frame 81 and the lower frame 82, and a handle 85 is provided on the upper frame 81. Moreover, at the both sides of the opened one side, a small double door 84 is provided.

A door claw 87 is provided at a distal end of a hinge 87 at a lower part of the door. Moreover, a hole is drilled in an outer portion where the hinge 87 at the lower part of the door is closed in the cassette lower frame 82, and a door lock pin 89 in which a stopper 90 is provided at an upper end and a lower end is fitted in the hole so as to be lowered freely by its own weight.

FIGS. 16A and 16B are partially enlarged side views showing a relation between the door lock pin 89 and the stopper 90. When the cassette 80 is placed on a flat-plate state table, as shown in FIG. 16A, the door lock pin 89 is pushed up, and the stopper 90 with an outer diameter larger than a shaft of the door lock pin 89 protrudes above the door claw 88. Since the shaft of the door lock pin 89 is thin, the door claw 88 is not engaged with the shaft but the door 84 can be freely opened/closed.

On the other hand, if the cassette 80 is lifted up, as shown in FIG. 16B, the pin 89 drops down. As a result, at the opening/closing operation, the door claw 88 of the door lower part 87 is engaged with the stopper 90 so as to prevent opening of the door 84. Also, a spring 90 is provided between the door lower part 87 and the cassette lower frame 82 so that the door 84 is urged in a direction of closing.

As a result, when the cassette 80 is placed on a flat table, the door 84 can be opened so that the microplate 95 can be freely inserted from the side face of a release portion 94 and stacked. When the cassette 80 is lifted up, the door lock pin 89 lowers and the door 84 is closed by the spring 92 so that the microplate does not fall to the release portion 92.

Also, at the rotating and containing table 43 on which the cassette 80 is set, a release hole (not shown) in which the door lock pin 89 is retreated when the cassette is placed is provided so that the door lock pin 89 is not released. Thereby, the door 84 will not open while the cassette is contained in the rotating and containing table 43, and the micro cassette 95 is prevented from falling from the side of the release portion 94.

On the bottom face of the cassette 80, a bottom-face opening 93 is provided, and a side-face opening 92 with the same degree as the bottom-face opening 93 even when the small door 84 is closed is present. Also, on the upper face of the cassette, an upper-face opening 94 to such a degree that the microplate 95 can be taken in and out is provided. As a result, the lift piece 46 of the plate elevation portion 45 can be raised upward through the bottom face 94 and the side-face opening 92 so that the microplate 95 can be taken out of the upper-face opening 94 or contained in the cassette.

The feeding and collecting portion 40 according to the present invention takes out or collects the microplate from the upper side of the cassette 80. Therefore, only by placing the cassette 80 on the rotating and containing table 43 provided at a low position lifted up from the floor only slightly, the cassette can be set in the rotating and containing table 43. In this way, there is no need to set the microplates 95 one by one in the feeding and collecting portion 40 but the microcassettes 95 can be replenished in the feeding and collecting device 40 only by setting by the unit of the cassettes 80. Also, when setting the cassette, there is no need to lift up a heavy cassette to a high position but it is only necessary that the cassette 80 is lifted up slightly and placed on the rotating and containing table 43, and the microplates can be replenished by an extremely lighter work than before.

[Dispensing Processing Device]

The dispensing processing will be described below in brief. The microplate main body portion 96 with the lid portion 98 removed and placed on the receiving/delivery table R2 is lifted up by a pickup portion (second pickup portion) of the dispensing device 70 and placed on the dispensing table 75. The pickup device (not shown) is provided at a distal end of a dispensing head 74 movable in X-, Y-, and Z-axis directions, which lifts up the microplate main body on the receiving/delivery table R2 and moves to the dispensing table 75.

The dispensing head 74 is mounted at a lower part of a movable member 73. The movable member 73 is provided at two movable frames 71 movable in the longitudinal direction (X-axis direction) along the conveying path, in the vertical direction (Z-axis direction) and a direction crossing the conveying path (Y-axis direction). Thereby, the dispensing head 74 is movable in all the X-, Y-, and Z-axis directions.

At the distal end of the dispensing head 74, dispensing pipettes (not shown) in the number corresponding to that of the wells 99 in the microplate are provided so that a drug solution is pumped up from a drug-solution tank 77 by the pipettes and then, the pumped-up drug solution is dispensed to the wells 99 in the microplate 95. Before the drug solution is pumped up, the pipette distal end of the dispensing head 74 is inserted into a pipette cassette 76, and a disposable pipette tip (not shown) is mounted at the distal end of the pipette. The pipette tip is automatically removed from the pipette distal end after the dispensing processing is finished and disposed of.

The microplate 95 for which the dispensing processing is finished is lifted up by the pickup device provided at the distal end of the dispensing head 75 and returned to the receiving/delivery table R2 or R3. The microplate 95 having been returned to the receiving/delivery table R2 or R3 is, similarly to the above-mentioned description, lifted up by the conveying table portion 12 of the shuttle conveying portion 11 and conveyed to the receiving/delivery table R1 or R4. The microplate 95 having been conveyed to the receiving/delivery table R2 is returned by the pickup device 50 to the feeding and collecting device 40, while the microplate having been conveyed to the receiving/delivery table R4 is conveyed by the horizontally rotating-type conveying robot 110 to the shelf 120, the analyzing device 130, and the humidity retaining device 140.

[Horizontally Rotating-type Robot and other Peripheral Equipment]

Figure 17:
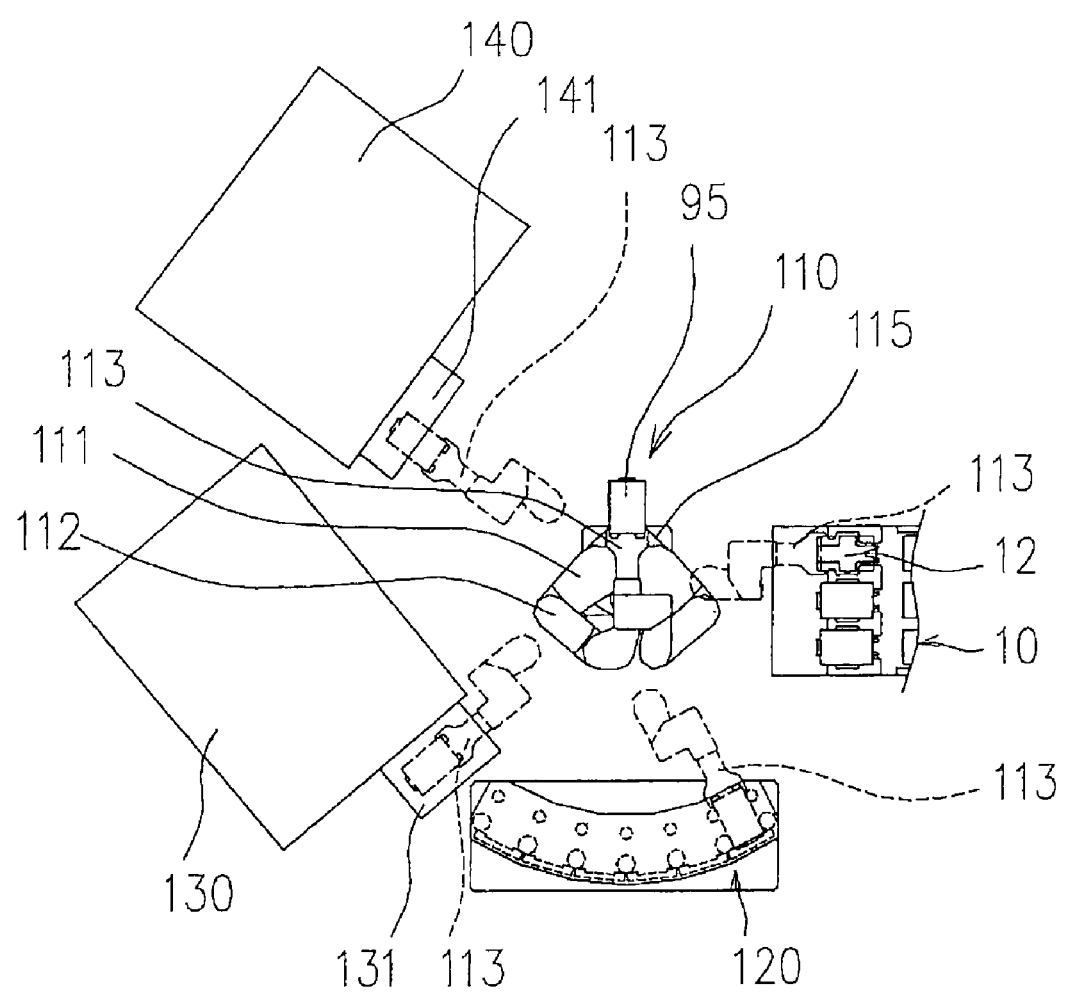
FIG. 17 is a plan view illustrating a conveying state of a horizontally rotating-type robot of the present invention.
Figure 18:
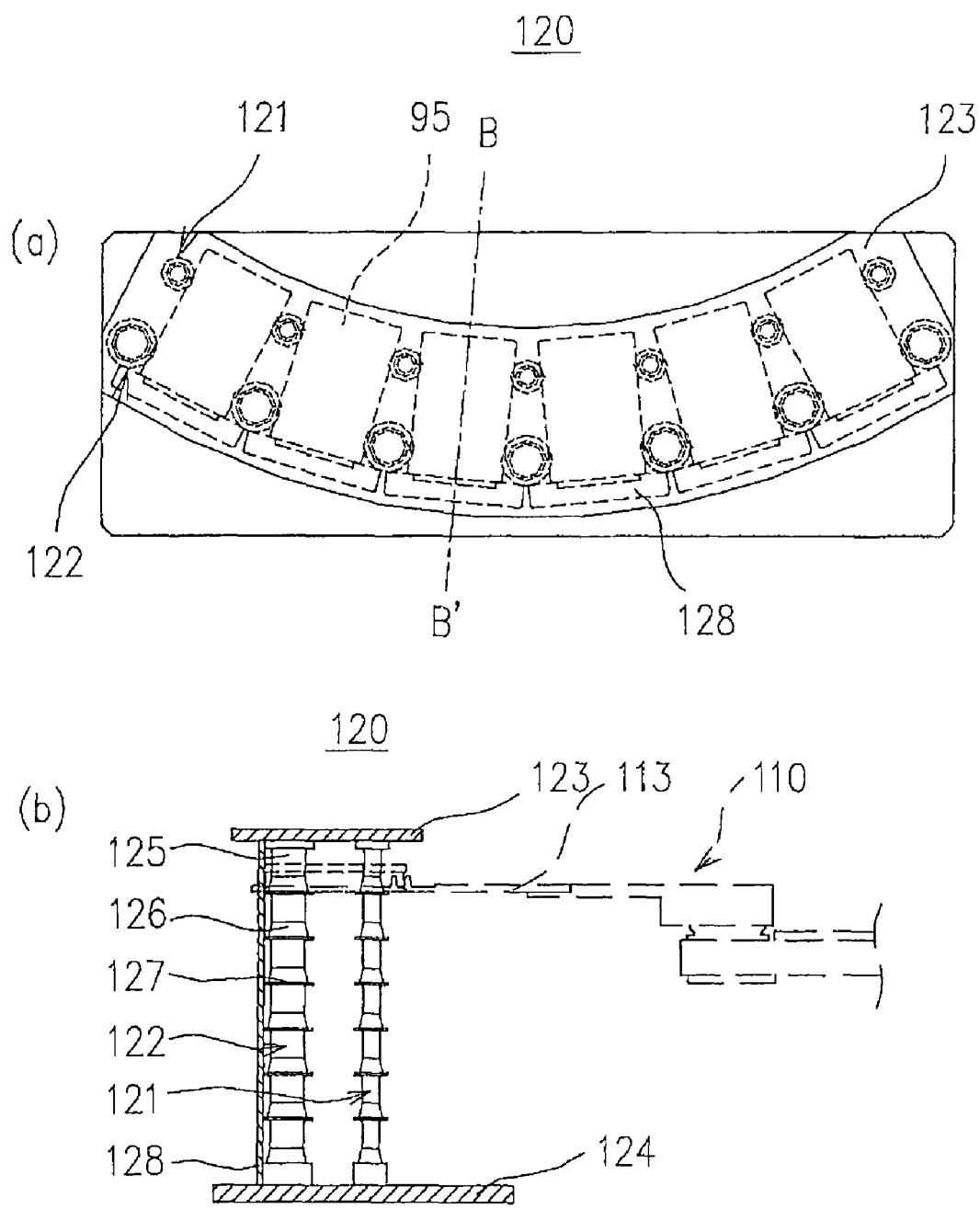
FIGS. 18 are plan view and side view of a containing shelf of the present invention.

FIG. 17 is a plan view illustrating a conveying state of the microplate 95 by the horizontally rotating robot 110. In this embodiment, as the horizontally rotating robot 110, a conveying robot RR 701 by Rorze Corporation is used. The horizontally rotating robot 110 has two arm bodies made of a first arm 111, a second arm 112, and fingers 113, each rotates in the respective horizontal planes, and the two ringers 113 make a straight motion horizontally in the same vertical plane overlapping with a height difference, while a trunk 115 makes a turning motion and a Z-axis elevation motion, and moreover, an X-axis orbit for moving the entire horizontally rotating robot 110 at a right angle with the shuttle-type conveying lines La to Lc is provided. However, the finger 113 is in a long rectangular shape in which six plastic bell-shaped projections with a height of 8 mm and a diameter of 6 mm are mounted on the periphery so that the microplate 95 placed on it does not drop or interfere with the receiving/delivery table R4. The horizontally rotating robot 110 is placed on the finger 113 such that the finger 113 is inserted below the receiving/delivery table R4 on which the microplate 95 is placed and the trunk 115 is lifted up in the Z-axis direction so as to scrape up the microplate 95. When conveying has reached the upper part of the target conveying table portion, the trunk 115 is lowered in the Z-axis direction, and the microplate 95 is placed on the target location from the finger 113. Here, the target location is any one of the shelf 120, an analyzing device sample entrance/exit 131, a warmer sample entrance/exit 141, and each stage 48.

The horizontally rotating robot 110 places the microplate 95 with a drug solution having been fed by the shuttle-type conveying device 10 on one of the fingers 113 as if to scrape up from below, makes a turn and goes toward the warmer 140. The microplate 95 of a sample having finished with a processing for a predetermined time and come out to the warmer sample entrance/exit 141 is placed on the other finger 113 and taken out, and the microplate 95 of a new sample having been conveyed is inserted instead. The warmer (Cytomat 6000) applies processing at a certain temperature for a predetermined time automatically even if the sample is automatically inputted by the unit of a box and carries out the sample by the unit of a box. Next, the robot makes a turn and goes toward the sample entrance/exit 131 of the analyzing device (1430 ViewLux I/F), extends the empty finger 113 so as to take out the analyzed sample microplate 95 and inserts the processed sample microplate 95 taken out of the warmer. Since the lid 192 of the microplate should be removed for analysis, the lid suction machine 28 is also provided at the analyzing device sample entrance/exit 131. The taken-out and analyzed sample microplate 95 is placed on the receiving/delivery table R4 of the shuttle-type conveying paths La to Lc. If the sample microplate 95 should wait for its turn of the warmer 140 or timing does not match between carrying-out of the warmer 140 and carrying-in to the analyzing device 130, the microplate 95 before processing is temporarily stored in the shelf 120 and analyzed when its turn comes.

FIG. 12A is a plan view illustrating a structure of the containing shelf 120 of the present invention. FIG. 12B is a sectional view at B-B' in FIG. 12A. Between the bottom board 124 and the top board 123, a plurality of thin inner columns (support columns) 121 and a plurality of thick outer columns (support columns) 122 in the same numbers are arranged in a concentric arc state. The shapes of the respective inner and outer columns for the one shelf stage are connected between a cylindrical column portion 125, a trapezoidal portion 126 and a flange portion 127 from the top, and on the upper face of the flange portion 127, an outer-edge corner portion of the bottom of the microplate 95 is placed. Therefore, a dimension between the circular trapezoidal portions 126 lower parts of the two inner columns 121 and a dimension between the circular trapezoidal portions 126 lower parts of the two outer columns 122 are the same and slightly longer than a width of the microplate 95, and an inter-central dimension between the inner column 121 and the outer column 122 is designed slightly shorter than the length of the microplate 95, on which one microplate 95 is placed. On the further outside of the outer column 122, a box stopper 128 for preventing passing through and drop of the microplate 95.

In this way, a plurality of projections are provided in intermediate portions of the columns 121, 122 in the containing shelf 120, and the microplate is supported by the projections between the support columns. Thus, by scraping up the microplate 95 contained in the containing shelf 120 by the finger 113 of the robot, the microplate can be easily taken out. Thus, as compared with taking-out by sandwiching the side face, control is simple and the microplate can be taken out rapidly and accurately.

Also, by providing projections in the middle of the support columns and only by connecting the top board and the bottom board by the support columns, the containing shelf 120 can be assembled. Thus, the number of parts is small and assembling is easy. Since the projection portions are integrally formed with the support column, a containing shelf with higher accuracy than assembling can be made easily.

The microplate 95 is inserted to the vicinity of the outer column 122 between the cylindrical column portions 125 of the two inner columns 121 of the containing shelf 120 in FIG. 12 while being mounted on the finger 113 of the horizontally rotating robot 110, and when the finger 113 is lowered, the four outer-edge corner portions on the bottom of the microplate 95 are placed on the flange portion 127. On the contrary, when the microplate 95 is to be taken out, the empty finger 113 is inserted between the two cylindrical column portions 125 and stopped so that the six plastic bell-shaped projections comes below outside the outer-edge portions of the microplate 95 and then, it is raised so that the microplate is placed, and the finger is pulled toward the robot 110 side. Then, the robot 110 conveys the microplate 95 to a target location.

[Conveying Control of the Microplate]

Figure 19:
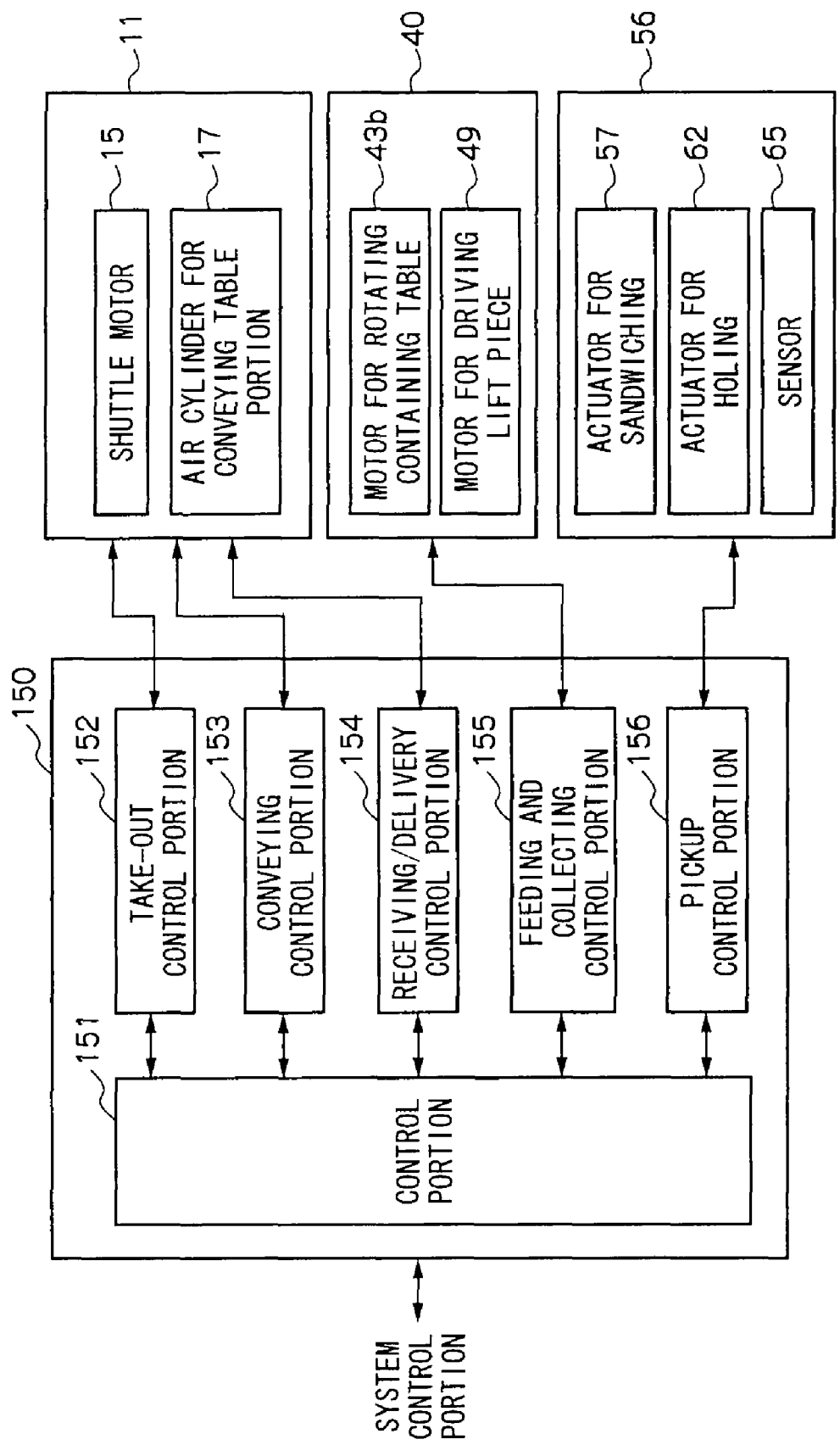
FIG. 19 is a basic functional block diagram illustrating an example of a controller for controlling the conveying device, pickup device for microplate, and the microplate feeding and collecting device of the present invention.

Each driving portion of the shuttle-type conveying device 10, the feeding and collecting device 40 and the pickup device 50 is controlled by a control portion. FIG. 19 shows a basic functional block diagram of a control device 150. The control device 150 is a computer provided with a central processing unit (CPU), a control program, a memory portion storing the control program, control data and the like, a logical circuit and the like, and by these control programs, according to a control command from system control of the analysis processing system, various operations are executed sequentially. In various operations, a feedback signal from various sensors (not shown) arranged at the conveying path, the shuttle conveying portion, and other portions are referred to.

The control device 150 is provided with a control portion 151 and communicates with the system control portion controlling the operation of the entire analysis processing system through a communication interface (not shown) and controls various operations of the shuttle conveying portion 11, the feeding and collecting portion 40, and the pickup portion 50 according to the command of the system control portion. The control device 150 is provided with a take-out control portion 152, a conveying control portion 153, a receiving/delivery control portion 154, a feeding and collecting control portion 155, and a pickup control portion 156 in addition to the control portion 151.

The take-out control portion 152 controls the shuttle motor 15 and the motor 17 for conveying table portion under control of the control portion 151 and controls the shuttle conveying portion 11 that lifts up the microplate (article to be conveyed) on the receiving/delivery tables R1 to R4 and takes it out. The conveying control portion 153 controls the shuttle motor 15 and the motor 17 for conveying table portion under the control of the control portion 151 and controls the shuttle conveying portion 11 that conveys the taken-out article to be conveyed to the target receiving/delivery tables R1 to R4. The receiving/delivery control portion 154 controls the shuttle motor 15 and the motor 17 for conveying table portion under the control of the control portion 151 and controls the shuttle conveying portion 11 so that the article to be conveyed on the conveying table portion is placed on the receiving/delivery tables R1 to R4 as transfer destinations.

The feeding and collecting control portion 155 controls driving of a motor 43b for rotation and driving that rotates and drives the rotating and containing table 43 and controls so that the microplate to be taken out is rotated and moved to the front of the plate elevation portion. Also, when the microplate 95 has been fed out of the cassette 80, the lift piece 46 is lifted up for one micro cassette, while when the microcassette 95 has been collected, the lift piece 46 is lowered by one micro cassette.

The pickup control portion 156 controls the actuator 57 for sandwiching of the pickup device 56 and the actuator 62 for holding under the control of the control portion 151 and sandwiches the side faces of the microplate 95 by the pair of sandwiching arms 59, 60 and holds it by the pair of holding arms 63 to lift it up.

[Conveying Processing Procedure Flowchart]

Figure 20:
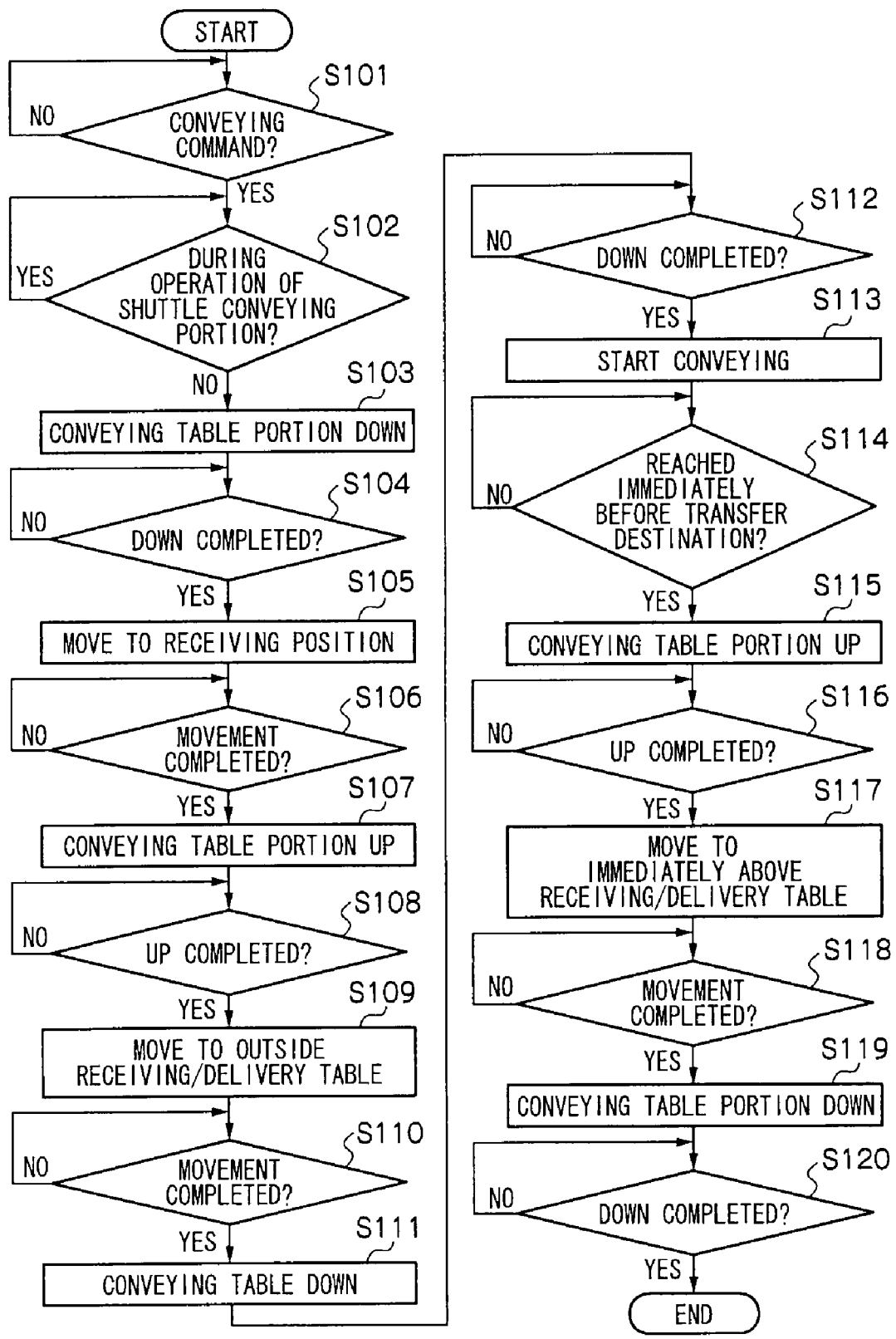
FIG. 20 is a flowchart illustrating an example of a conveying control processing procedure of an article to be conveyed by the shuttle-type conveying device of the present invention.

Using FIG. 20, an example of a conveying processing procedure of an article to be conveyed will be described. FIG. 20 is a flowchart illustrating the conveying control processing procedure of the article to be conveyed by the shuttle-type conveying device of the present invention. In the flowchart, raising completion and lowering completion of the conveying table portion and various conveying positions are confirmed. These confirmations can be made by a driving time of each driving portion and a feedback signal, but it is preferable that various sensors are further provided at each portion of the conveying path and the shuttle conveying portion and the like so that confirmation is made by a sensor signal. The control portion 151 checks if a conveying command has been received or not, and if the conveying command is received (S101: Yes), it checks if the shuttle conveying portion 11 is during operation or not (S102). If the shuttle conveying portion 11 is not in operation (S102: No), the conveying table portion 12 of the shuttle conveying portion is lowered (S103). When the lowing of the conveying table portion 12 is completed (S104: Yes), the shuttle conveying portion 11 is moved to the receiving/delivery tables R1 to R4 on which the article to be conveyed is placed (S105).

When the shuttle conveying portion 11 has moved immediately below the target receiving/delivery table (S106: Yes), the conveying table portion 12 is raised and the article to be conveyed is lifted up by the conveying table portion 12 from below the receiving/delivery table (S107). When the raising of the conveying table portion 12 is completed (S108), the shuttle conveying portion 11 is moved outside the receiving/delivery table with the article to be conveyed lifted up (S109), and when the movement is completed (S110: Yes), the conveying table portion 12 is lowered with the article to be conveyed on (S111). At this time, it is determined by the control portion 151 if there is no obstacle up to the transfer destination such that the transfer destination is the adjacent receiving/delivery table and the like, and if there is no obstacles, Steps S111 and S112 can be skipped.

When lowering of the conveying table portion 12 is completed (S112: Yes), movement of the shuttle conveying portion 11 is started (S113). The shuttle conveying portion 11 is passed through and moved below the receiving/delivery table with the article to be conveyed placed on the conveying table portion 12. When the shuttle conveying portion 11 has moved next to the receiving/delivery table to be the designated conveying destination (S114: Yes), the conveying table portion 12 is raised (S115). When the raising of the conveying table portion 12 is completed (S116: Yes), the shuttle conveying portion 11 is moved immediately above the receiving/delivery table (S117). When the movement is completed (S118: Yes), the operation table portion 12 is passes through the bottom-face opening portion 23 and lowered to below the receiving/delivery table (S119). When the lowering of the operation table portion 12 is completed, the conveying processing is finished, and the next conveying command is awaited.

In the above description, only the example in which the microplate is conveyed as the article to be conveyed by the shuttle-type conveying device has been described, but this is an example of the article that can be conveyed by the shuttle-type conveying device according to the present invention and not limited to the microplate but any article having a given width that can be placed on the receiving/delivery table of the present invention and can be placed on the conveying table portion of the shuttle conveying portion can be conveyed.

When an article other than the micro cassette is to be conveyed, the structure of the conveying table portion 12 and the structures of the elevating device and the driving device can be changed as appropriate by a known art according to a weight of the article to be conveyed. For example, if the weight is heavy, the article can be lifted up using a hydraulically driven piston. It is only necessary that the elevating device for elevating the conveying table portion can take two positions of a high position and a low position. The high position is a position where the conveying table portion 12 lifts up the article to be conveyed such as the microplate 95 and the like over the receiving/delivery tables R1 to R4, while the low position is a position where the article to be conveyed is held at a position lower than the receiving/delivery tables R1 to R4 to be run below the receiving/delivery tables R1 to R4.

As driving means for moving the shuttle conveying portion 11 on the conveying paths La, Lb, Lc, known conventional arts available to those skilled in the art such as a stepping motor, a linear motor, an ultrasonic motor and the like can be used.

The invention claimed is:
1. A shuttle-type conveying device comprising:
   at least one conveying path;
   a shuttle conveying portion provided with a conveying table portion that can be elevated up and down for reciprocating or circulating on the conveying path with an article to be conveyed on the conveying table portion;
   a receiving/delivery table arranged above the conveying path and provided with a bottom-face opening portion larger than the conveying table portion and smaller than the article to be conveyed; and a control portion for controlling the shuttle conveying portion so that the article to be conveyed which is placed on the receiving/delivery table is taken out, conveyed and placed on the receiving/delivery table at a conveying destination by movement on the conveying path of the shuttle conveying portion and an elevating operation of the conveying table portion;

a take-out control portion that moves the shuttle conveying portion to below the receiving/delivery table with the conveying table portion lowered and raises the conveying table portion from below the receiving/delivery table and has it passed through the bottom-face opening portion, thereby to lift up the article to be conveyed placed on the receiving/delivery table;

a conveying control portion for moving the conveying table portion with the article to be conveyed to the receiving/delivery table to be a conveying destination; and a receiving/delivery control portion that moves the shuttle conveying portion with the article to be conveyed to above the bottom-face opening portion of the receiving/delivery table to be the conveying destination and then, lowers the conveying table portion so that the article to be conveyed is placed on the receiving/delivery table of the conveying destination;

a receiving/delivery control portion that moves the shuttle conveying portion with the article to be conveyed to above the bottom-face opening portion of receiving/delivery table to be the conveying destination and then, lowers the conveying table portion so that the article to be conveyed is placed on the receiving/delivery table of the conveying destination, and that moves the shuttle conveying portion to outside the receiving/delivery table after the article to be conveyed is lifted up by the taken-out control portion, and then, lowers the conveying table portion at a position lower than the receiving/delivery table, has the shuttle conveying portion with the article to be receiving/delivery table to be a conveying destination.

2. The shuttle-type conveying device according to claim 1, wherein a work table is provided over the conveying path so as to bridge over the conveying path, and when the shuttle conveying portion passes and moves below the work table, the article to be conveyed is conveyed to the receiving/delivery tables provided on upstream and downstream sides of the conveying path with the work table between them.

\* \* \* \* \*